United States Patent
Mandal et al.

(10) Patent No.: US 9,863,246 B2
(45) Date of Patent: Jan. 9, 2018

(54) METHODS AND APPARATUS FOR OIL SAMPLE ANALYSIS USING J-EDIT NUCLEAR MAGNETIC RESONANCE

(71) Applicant: SCHLUMBERGER TECHNOLOGY CORPORATION, Sugar Land, TX (US)

(72) Inventors: Soumyajit Mandal, Cambridge, MA (US); Yi-Qiao Song, Newton Center, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 867 days.

(21) Appl. No.: 14/149,537

(22) Filed: Jan. 7, 2014

(65) Prior Publication Data

US 2015/0192011 A1     Jul. 9, 2015

(51) Int. Cl.
| | | |
|---|---|---|
| E21B 49/08 | (2006.01) | |
| G01V 3/32 | (2006.01) | |
| G01N 33/28 | (2006.01) | |
| E21B 49/10 | (2006.01) | |

(52) U.S. Cl.
CPC ............ *E21B 49/087* (2013.01); *E21B 49/10* (2013.01); *G01N 33/28* (2013.01); *G01V 3/32* (2013.01)

(58) Field of Classification Search
CPC ........ E21B 49/087; G01N 33/28; G01V 3/32; G01R 33/3808
See application file for complete search history.

(56) References Cited

U.S. PATENT DOCUMENTS

| | | | |
|---|---|---|---|
| 6,140,817 A | 10/2000 | Flaum et al. | |
| 6,815,950 B2* | 11/2004 | Speier | G01N 24/081 324/300 |
| 6,958,604 B2 | 10/2005 | An et al. | |
| 7,532,007 B2* | 5/2009 | Song | G01V 3/32 324/303 |
| 7,637,151 B2* | 12/2009 | Raghuraman | G01N 33/2823 250/255 |
| 8,471,559 B2 | 6/2013 | Taherian et al. | |
| 9,140,657 B2* | 9/2015 | Ledbetter | G01N 24/08 |
| 2004/0257075 A1* | 12/2004 | An | G01V 3/32 324/303 |
| 2012/0169334 A1 | 7/2012 | Hopper et al. | |

(Continued)

OTHER PUBLICATIONS

Garbow, et al., "Bilinear rotation decoupling of homonuclear scalar interactions", Chemical Physics Letters, vol. 93, Issue 5, Dec. 17, 1982, pp. 504-509.

(Continued)

*Primary Examiner* — Gregory H Curran
(74) *Attorney, Agent, or Firm* — Michael Dae

(57) ABSTRACT

A hydrocarbon sample is subjected to a chemically selective J-editing nuclear magnetic resonance (NMR) pulse sequence. Resulting signals are analyzed in order to identify a coupling frequency present in at least one molecule of the hydrocarbon sample. A J-coupling frequency of approximately 150 Hz is indicative of a component having an internal double bonded carbon atom (i.e., an olefin). The presence of an olefin in a hydrocarbon sample can be indicative of the presence of a synthetic based mud (SBM) in the sample.

22 Claims, 19 Drawing Sheets

(56) References Cited

U.S. PATENT DOCUMENTS

2013/0257425 A1* 10/2013 Struppe .............. G01R 33/4608
324/309

OTHER PUBLICATIONS

Schnall, et al., "A new double-tuned probed for concurrent 1H and 31P NMR", Journal of Magnetic Resonance, vol. 65, Issue 1, 1969, pp. 122-129.
Wimperis, et al., "An excitation sequence which discriminates between direct and long-range CH coupling", Journal of Magnetic Resonance, vol. 58, Issue 2, Jun. 15, 1984, pp. 348-353.
Hahn, et al., "Spin Echo Measurements of Nuclear Spin Coupling in Molecules", Physical Review, vol. 88, 1952, pp. 1070-1084.
Hurlimann, "Diffusion and relaxation effects in general stray field NMR experiments", Journal of Magnetic Resonance, vol. 148, 2001, pp. 367-378.
Hurlimann, et al., "Quantitative Measurement of Two-Dimensional Distribution Functions of Diffusion and Relaxation in Grossly Inhomogeneous Fields", Journal of Magnetic Resonance vol. 157, No. 1, Jul. 2002, pp. 31-42.
Jenista, et al., "Optimized, unequal pulse spacing in multiple echo sequences improves refocusing in magnetic resonance", The Journal of Chemical Physics, vol. 131, No. 20, Nov. 2009, pp. 204510-204517.
Neff, et al., "Environmetnal Impacts of Synthetic Based Drilling Fluids", OCS Study MMS 2000-064—U.S. Department of the Interior Minerals Management Service, Gulf of Mexico OCS Region, 2000, 132 pages.

* cited by examiner

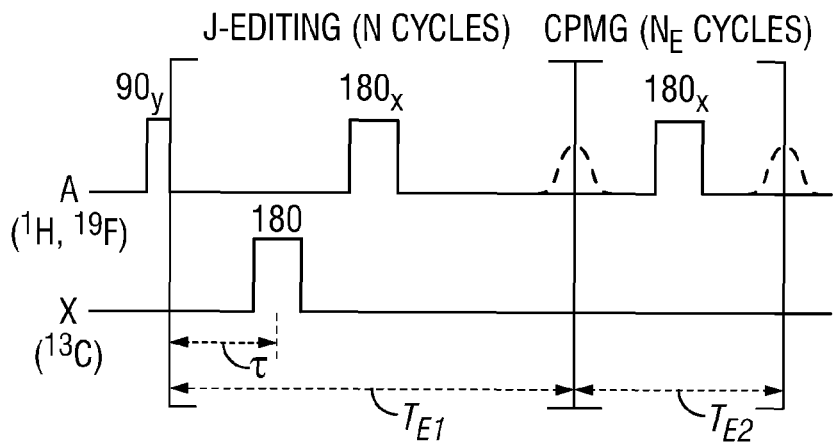
FIG. 1
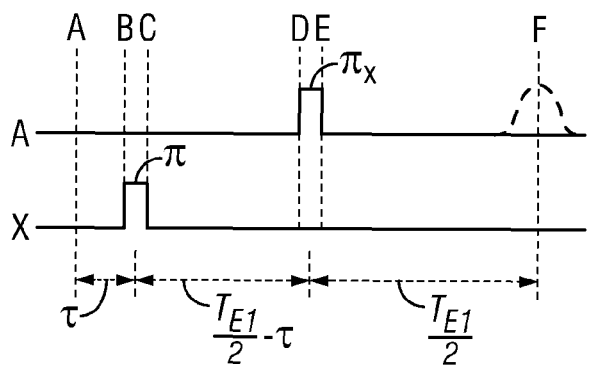
FIG. 2A
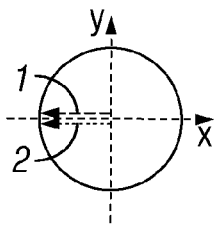 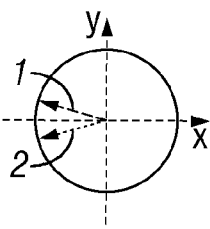 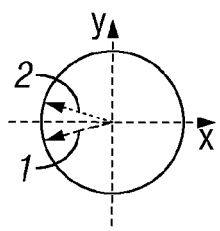
FIG. 2B　　　　　FIG. 2C　　　　　FIG. 2D
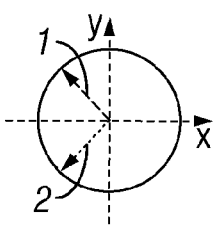 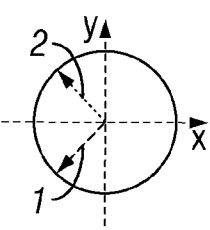 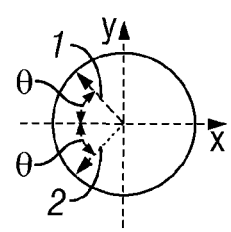
FIG. 2E　　　　　FIG. 2F　　　　　FIG. 2G

| Type | Chemical structure |
|---|---|
| Synthetic hydrocarbons | |
| Linear Alpha Olefin (LAO) | $CH_3\text{-}(CH_2)_n\text{-}CH=CH_2$ |
| Poly Alpha Olefin (PAO) | $CH_3\text{-}(CH_2)_n\text{-}C=CH\text{-}(CH_2)_m\text{-}CH_3$ <br> $\quad\quad\quad\quad\quad\; \backslash (CH_2)_p\text{-}CH_3$ |
| Internal Olefin (IO) | $CH_3\text{-}(CH_2)_m\text{-}CH=CH\text{-}(CH_2)_n\text{-}CH_3$ |
| Linear Alkyl Benzene (LAB) | $CH_3\text{-}CH\text{-}(CH_2)_n\text{-}CH_3$ <br> $\quad\quad\;\; |$ <br> $\quad\quad\;\; \bigcirc$ |
| Other synthetic base chemicals | |
| Ether | $CH_3\text{-}(CH_2)_n\text{-}O\text{-}(CH_2)_n\text{-}CH_3$ |
| Ester | $CH_3\text{-}(CH_2)_n\text{-}C=O$ <br> $\quad\quad\quad\quad\quad \backslash O\text{-}(CH_2)_m\text{-}CH_3$ |
| Acetal | $CH_3\text{-}(CH_2)_n\text{-}O \quad O\text{-}(CH_2)_n\text{-}CH_3$ <br> $\quad\quad\quad\quad\quad \backslash\;\;/$ <br> $\quad\quad\quad\quad\quad CH\text{-}(CH_2)_m\text{-}CH_3$ |

FIG. 5

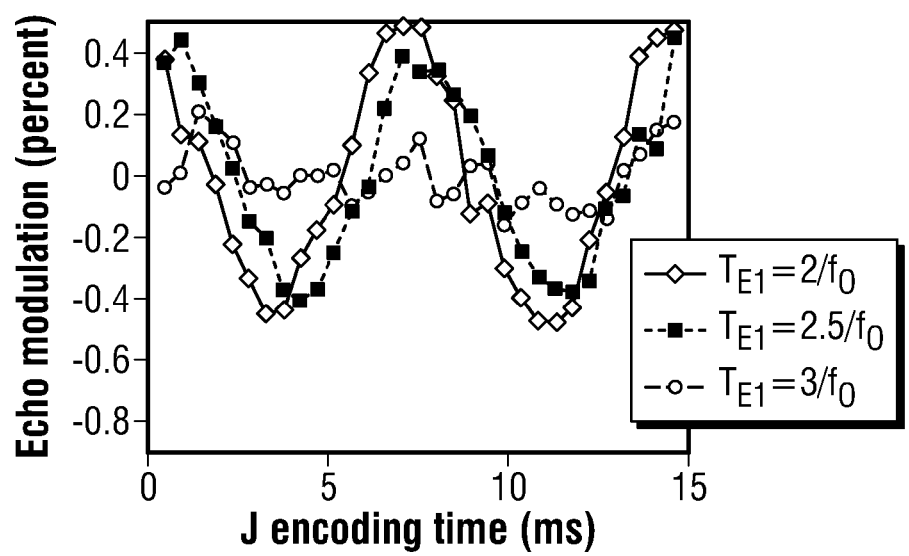

FIG. 6

METHODS AND APPARATUS FOR OIL SAMPLE ANALYSIS USING J-EDIT NUCLEAR MAGNETIC RESONANCE

FIELD

The subject disclosure relates to the oilfield. The subject disclosure more particularly relates to nuclear magnetic resonance (NMR) methods and apparatus utilizing J-editing for analysis of oil samples.

BACKGROUND

Oil and gas exploration and production are expensive operations. Knowledge about the formations that can help reduce the unnecessary waste of resources in exploration, well drilling, and production is valuable. Therefore, the oil and gas industry has developed various tools capable of determining and predicting earth formation properties. Nuclear magnetic resonance (NMR) instruments are among the tools utilized by the industry. NMR instruments can be used to determine formation properties, such as the fractional volume of pore space and the fractional volume of mobile fluid filling the pore space. General background of NMR well logging is described in U.S. Pat. No. 6,140,817 issued on Oct. 31, 2000, which is hereby incorporated by reference herein in its entirety.

Nuclear magnetic resonance is a phenomenon occurring in a selected group of nuclei having magnetic nuclear moments, i.e., non-zero spin quantum numbers. When these nuclei are placed in a magnetic field ($B_0$, "Zeeman field"), they precess around the axis of the $B_0$ field with a specific frequency, the Larmor frequency ($\omega_0$), which is a characteristic property of each nuclear species (gyromagnetic ratio, $\gamma$) and depends on the magnetic field strength ($B_0$) effective at the location of the nucleus, i.e., $\omega_0 = \gamma B_0$.

A proton ($^1$H) is the major nucleus of investigation in well logging NMR applications because of its good NMR sensitivity and its high abundance in water and hydrocarbons. However, other nuclei, such as carbon ($^{13}$C isotope only, with a natural abundance of 1.1%) also provide NMR signals which can be used to obtain additional information about the sample. In NMR applications, proton and carbon chemical shift and J-coupling spectroscopic techniques may be used to determine molecular structures. Chemical shift is the term given to describe the screening effect of the electrons to the magnetic field that a nucleus experiences. Different chemical groups, such as $CH_2$ and $CH_3$, have different magnitude of screening effects, and, therefore, they appear as separate peaks in the proton chemical shift spectrum. The separation in frequency of different peaks is proportional to the static magnetic field strength, i.e., magnetic field dependent. On the other hand, J-coupling, which is also known as spin-spin or scalar coupling, originates from spin interaction between nuclei through bonding electrons and does not depend on the static magnetic field strength. See, E. L. Hahn, and D. E. Maxwell, Spin echo measurements of nuclear spin coupling in molecules, Physical Review 88, 1070-1084 (1952).

The use of J-editing NMR measurements is disclosed in co-owned U.S. Pat. No. 6,958,604 issued on Oct. 25, 2005 to An et al., which is hereby incorporated by reference herein in its entirety. As disclosed in An et al., one method for obtaining nuclear magnetic resonance measurements includes inducing a static magnetic field in a formation fluid sample, applying an oscillating magnetic field to the fluid sample according to a preparation pulse sequence that comprises a J-edit pulse sequence for developing J modulation, and acquiring the nuclear magnetic resonance measurements using a detection sequence, wherein the detection sequence comprises at least one 180-degree pulse. The method may further include acquiring the nuclear magnetic resonance measurements a plurality of times each with a different value in a variable delay in the J-edit pulse sequence, and analyzing amplitudes of the plurality of nuclear magnetic resonance measurements as a function of the variable delay to provide J coupling information.

The "Fermi contact mechanism" is generally considered to be responsible for J-coupling between nuclear spins. It relies on the fact that an electron in a chemical bond X—Y spends a certain amount of time at the same point in space as, say, nucleus X. In other words, the hybrid orbital (wave function describing the bonded electron) has non-zero amplitude at that location. Thus, if nucleus X has a spin $I_z = +1/2$, the Pauli exclusion principle results in the electron spin being $-1/2$. The principle also has two more effects. First, the second bonding electron must have spin $+1/2$. Second, nucleus Y can only occupy the same point in space as the second bonding electron if its spin is $I_z = -1/2$. The net effect is that whenever nucleus X has spin $+1/2$, it is slightly more energetically favorable for nucleus Y to have spin $-1/2$. The two nuclei are then said to have a positive one-bond J-coupling constant. The coupling mechanism can extend over multiple bonds, although it weakens rapidly as the number of bonds increases.

Isotropic J-coupling is not averaged out by molecular motion, since it relies on bonding electrons. Hence it is also known as scalar coupling. Some interesting properties of J-coupling can be derived from hybrid orbital theory. Hybrid orbitals are formed when several atomic orbitals mix together during the formation of molecules. For example, only electrons in s-type atomic orbitals can contribute to the Fermi contact mechanism, since p-orbitals have zero amplitude (nodes) at the locations of nuclei. Thus the J-coupling strength increases as the s-character of the bond increases. In fact, it depends on the product of the s-characters of the hybrid orbitals from both nuclei that form the bond. It is also proportional to the product of the gyromagnetic ratios of the two bonded nuclei.

Considering $^1$H—$^{13}$C one-bond couplings, the proton binding orbital is derived from a single $^1$s orbital and has a 100% s character. However the carbon binding orbital is derived from one s-type ($^2$s) and three p-type ($^2p_x$, $^2p_y$, and $^2p_z$) orbitals, and can be hybridized in different ways depending on the molecule, such as $sp^3$ (25% s), $sp^2$ (33% s), and sp (50% s). It has been empirically found that in many organic molecules the single-bond $^1$H—$^{13}$C J-coupling strength is linearly proportional to the fraction of s-character in the bond:

$$J(C-H)[Hz] \approx 5[\% \, s(C-H)] \quad (1)$$

This simple rule predicts J-coupling values of simple non-polar molecules quite well, as shown in Table 1 below:

TABLE 1

| Molecule | Hybridization | Predicted (Hz) | Measured (Hz) |
|---|---|---|---|
| Methane | $sp^3$ | 125 | 125 |
| Ethylene | $sp^2$ | 165 | 157 |
| Benzene | $sp^2$ | 165 | 159 |
| Acetylene | sp | 250 | 249 |

Aromatic and double-bonded groups have similar properties because the carbon atom is $sp^2$ hybridized in both cases.

Additional complications occur for polar molecules. For example, methanol has a single-bond H—C J-coupling frequency of 141 Hz (the J-coupling energy and J-coupling frequency being related by Planck's constant, as is well-known, with the terms being used interchangeably), which is in between the expected values for sp$^3$ and sp$^2$ hybridization. Overall, single-bond $^1$H—$^{13}$C coupling strengths range between 100 Hz and 320 Hz.

C—H J-coupling in hydrocarbons only affects those atoms bound to $^{13}$C, i.e., approximately 1.1% of the total proton signal. It consists of components at several frequencies. The dominant component at a coupling frequency of 125 Hz corresponds to protons attached to single-bonded carbon atoms, which are sp$^3$-hybridized. Smaller components around 157 Hz correspond to protons attached to aromatic rings and terminal double bonds, which are sp$^2$-hybridized. These values are very similar to the prototypical sp$^3$ and sp$^2$ hybridized molecules shown in Table 1.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one embodiment, a method for analyzing an oil sample includes inducing a static magnetic field in a formation fluid sample, applying an oscillating magnetic field to the fluid sample according to a J-editing pulse sequence incorporating a chemically selective excitation pulse that preferentially selects spins satisfying particular conditions while suppressing other spins (i.e., a J-filter), and making measurements by detecting a resulting signal and processing the resulting signal. In one embodiment, the J-editing pulse sequence with chemically selective excitation is an A spin (such as $^1$H) pulse sequence of $(\pi/4)_x$-$\tau'$-$(\pi)_y$-$\tau'$-$(3\pi/4)_{-x}$-$T_{E1}/2$-$(\pi)_x$-$T_{E1}/2$-$(T_{E2}/2$-$(\pi)_x$-$T_{E2}/2)_N$, and an X spin (such as $^{13}$C) pulse sequence of $(\pi)$ concurrent with the $(\pi)_y$ pulse of the A spin and a $(\pi)$ pulse at time r within the first $T_{E1}/2$ period of the A spin. The $\tau$ of the X spin is the J-encoding time and may be varied, and $\tau'$ is a function of the filter frequency and may be varied. Carr-Purcell-Meiboom-Gill (CPMG)-type detection is conducted at intervals of $T_{E2}$ around the repeated $(\pi)_x$ signals. In another embodiment, the J-editing pulse sequence with chemically selective excitation is an A spin (such as $^1$H) pulse sequence of $T_{E1}/2$-$(\pi)_x$-$T_{E1}/2$-$(T_{E2}/2$-$(\pi)_x$-$T_{E2}/2)_N$, and an X spin (such as $^{13}$C) narrow-band pulse of $(\pi)$ concurrent with the $(\pi)_y$ pulse of the A spin, where the narrow-band pulse is tuned to a desired frequency.

In one embodiment a method for analyzing an oil sample includes inducing a static magnetic field in a formation fluid sample, applying an oscillating magnetic field to the fluid sample according to a J-editing pulse sequence, and making measurements by detecting a resulting signal and processing the resulting signal in order to determine whether any J-encoding time signal at or about 150 Hz is detected. In one aspect, if a J-encoding time signal at 150 Hz is detected, the presence of a hydrocarbon having internal double bonds (e.g., olefin) is indicated. In one aspect, the presence of an olefin in an oil sample taken from a formation can be indicative of the presence of synthetic oil based mud (SBM) in the sample.

In one embodiment, the J-editing pulse sequence used as part of a method for determining whether any J-encoding time signal at or about 150 Hz is detected is a J-editing pulse sequence incorporating a chemically selective excitation pulse.

In one embodiment, a method for analyzing an oil sample includes utilizing a J-editing pulse sequence that includes J-modulation scans with interleaved reference scans.

BRIEF DESCRIPTION OF THE DRAWINGS

FIG. 1 shows a two channel "J-editing" pulse sequence with CPMG detection.

FIGS. 2A-2G show a pulse sequence and vector model of a single J-editing cycle.

FIG. 5 is a chart of the names and chemical structure of various synthetic hydrocarbons and synthetic base chemicals.

FIG. 6 is a plot of measured J-modulation curves of dodecane for various values of the initial echo period $T_{E1}$.

DETAILED DESCRIPTION

Figure 3A:
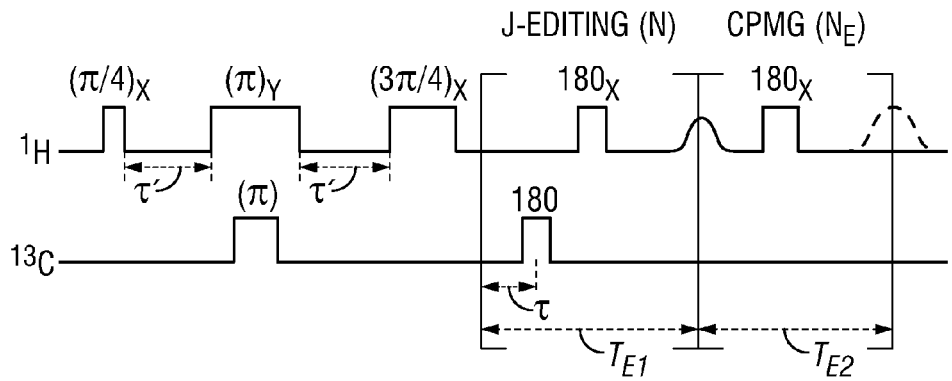
FIGS. 3A and 3B show two different chemically-selective J-editing pulse sequences.

As mentioned previously, C—H J-coupling in hydrocarbons affects those hydrogen nuclei (protons) bound to $^{13}C$ and includes components at several frequencies. The dominant component at a coupling frequency of 125 Hz corresponds to protons attached to single-bonded carbon atoms, which are $sp^3$-hybridized while smaller components at a coupling frequency around 157 Hz correspond to protons attached to aromatic rings and terminal double bonds, which are $sp^2$-hybridized. Protons attached to internal double bonds have been found to have slightly lower J-coupling values (approximately 149 Hz) than expected for $sp^2$-hybridized carbons, perhaps because carbon atoms that form an internal C=C double bond also form a C—C single bond. These two types of bonds hybridize to some extent, effectively weakening the double bond and the resultant C—H J-coupling. These three components are sufficient to describe the J-coupling spectra of most hydrocarbon molecules.

FIG. 1 shows a "J-editing" pulse sequence with Carr-Purcell-Meiboom-Gill (CPMG) detection suitable for measuring heteronuclear J-coupling constants in inhomogeneous fields. In this sequence, sensitive A spins (such as $^1H$ and $^{19}F$) are the source of magnetization and the subject of detection (in the CPMG cycle), while X spins (such as $^{13}C$) are flipped by π (180 degree) pulses during the initial N refocusing cycles to enable the buildup of J-modulation. More particularly, transmitter channel A is shown with a π/2(y) pulse followed by a π(x) pulse at time $T_{E1}/2$ for N cycles, followed by a CPMG sequence with detection and π(x) pulses, while the transmitter channel X is shown with a single it pulse. The location of this π pulse within each cycle is defined by a variable time delay τ (the "J-encoding time"), as shown in FIG. 1. The effect of these pulses can be qualitatively understood using an extension of the vector model commonly used to describe uncoupled spin-1/2 systems. The effect of J-coupling in this model is to split the magnetization vector into two components. The first component rotates faster than the uncoupled magnetization vector on the x-y plane (by an amount +J/2), while the second component rotates slower by the same amount. It can be assumed that the π pulses only have enough bandwidth to invert one of the coupled spins (either A channel or X channel). This is usually an excellent approximation for heteronuclear couplings, since the Larmor frequency difference between dissimilar nuclei is usually much greater than $\omega_1 = \gamma B_1$. Here $B_1$ is the amplitude of the radio frequency (RF) magnetic field during pulses. Thus π pulses on either channel invert the sign of the coupling term in the Hamiltonian, effectively flipping the labels on the two J-coupled vectors. The resultant evolution of the magnetization during one refocusing cycle for the particular case $\tau = T_{E1}/8$ is shown in FIGS. 2A-2G where the vectors rotate clockwise and anti-clockwise respectively relative to the uncoupled spins which remain fixed along the x-axis. The chemical shift evolution may be ignored since it is refocused by the t pulses.

It is evident from FIGS. 2A-2G that the angle θ made by either J-coupled vector with the refocusing axis (x-axis) at the end of a single cycle is given by $$\theta = (\tau)\frac{2\pi J}{2} - \left(\frac{T_{E1}}{2} - \tau\right)\frac{2\pi J}{2} + \left(\frac{T_{E1}}{2}\right)\frac{2\pi J}{2} = 2\pi J\tau \quad (2)$$

The process continues for N cycles, increasing the angle to Nθ. The refocused J-coupled signal is then proportional to the projection of both vectors onto the refocusing axis, i.e., $\cos(N\theta) = \cos(2\pi J N\tau)$. Thus, the magnetization is allowed to evolve due to J-coupling at a rate $2\pi J$ during an encoding time of Nτ. This process is analogous to the way diffusion is encoded in diffusion-editing sequences, hence the term "J-editing." The analysis is also valid when C—H bonds with different J-coupling constants are present in the sample. Each bond will evolve independently according to its own coupling constant, so the total signal can be found simply by adding the corresponding frequency components.

An advantage of the sequence shown in FIG. 1 is that the echo-spacing $T_{E1}$ is kept fixed with τ, which simplifies data analysis by keeping relaxation and diffusion effects constant. The frequency resolution $\Delta f \approx 1/(N\tau_{max}) > 2/(NT_{E1})$ can be increased by increasing the maximum J-encoding time $N\tau_{max}$, where $\tau_{max} < T_{E1}/2$. The J-editing cycles are followed by a train of $N_E$ refocusing pulses (CPMG), which refocus the heteronuclear J-couplings, thereby preventing further J-modulation. The refocusing pulses also generate multiple spin echoes that can be added together to increase SNR. Neglecting field inhomogeneity effects, the previous analysis shows that the asymptotic CPMG echo amplitude S(Nτ) is given by $$S(N\tau) = a_0 + \sum_{i=1}^{M} a_i \cos(2\pi J_i N\tau), \quad (3)$$

where $a_i$ is the fractional abundance of A-X bonds with coupling constant $J_i$, M is the number of unique coupling constants, and $a_0$ is the background signal due to uncoupled A spins. The shape of this J-modulation curve can be analyzed to distinguish between different carbon groups, such as aliphatics and aromatics, that have significantly different J-coupling constants. It can also be used to compute the hydrogen index and hydrocarbon/water ratio of fluid samples.

Figure 3B:
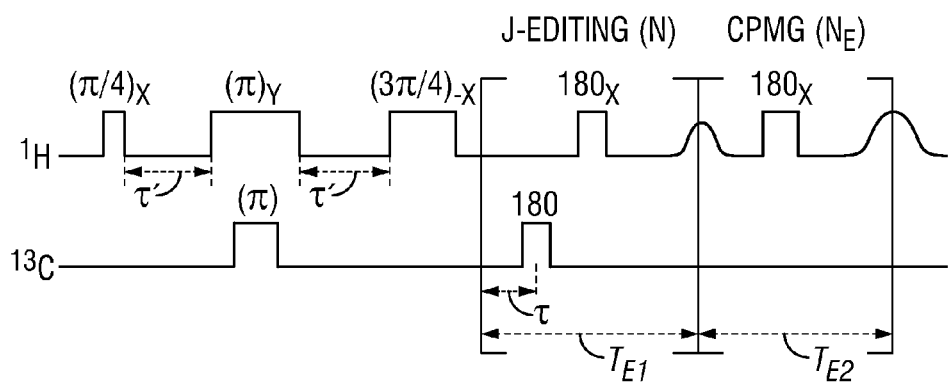

According to one aspect, and as seen in FIGS. 3A and 3B, the J-editing pulse sequence of FIG. 1 may be modified to make the pulse sequence chemically selective. Thus, in FIGS. 3A and 3B, the initial π/2(y) pulse of the A channel (of FIG. 1) is replaced by either of two sequences: (π) a π/4(x) pulse followed by a π(y) pulse after time τ', followed by a 3π/4(x) pulse after additional time τ' on the A channel, and a it pulse on the X channel at the time of the A channel's π(y) pulse; or (ii) a π/4(x) pulse followed by a π(y) pulse after time τ', followed by a 3π/4(-x) pulse after additional time τ' on the A channel, and a it pulse on the X channel at the time of the A channel's π(y) pulse. More particularly, precession due to single-bond J-coupling can be used to distinguish between protons that are chemically bonded to NMR-active nuclei (such as $^{13}C$ or $^{15}N$) and those that are not. In FIG. 3A, the pulse sequence of a $\pi/4(x)$ pulse followed by a $\pi(y)$ pulse after time $\tau'$, followed by a $3\pi/4(x)$ pulse after additional time $\tau'$ on the A channel behaves as a 90-degree (excitation) pulse when $\tau'=1/(2J)$ for protons that are not chemically bonded to $^{13}C$ atoms, while acting as a 360-degree (identity) pulse for bonded protons. As a result, protons bonded to $^{12}C$ (which has zero spin and is NMR-silent) will be selectively observed, while protons bonded to $^{13}C$ will be suppressed. The pulse sequence of FIG. 3B which differs from the pulse sequence of FIG. 3A only in the phase of the $3\pi/4$ proton pulse, reverses the roles of these two groups; i.e., the protons bonded to $^{13}C$ will be selectively observed while the protons bonded to $^{12}C$ will be suppressed. Thus the pulse sequence of FIG. 3B advantageously combines the J-editing sequence of FIG. 1 with a selective excitation pulse sequence that suppresses the unmodulated background signal from protons attached to $^{12}C$ atoms. The result is an increase in the fractional amount of J-modulation. This provides increased robustness to multiplicative error sources such as drifts in temperature and preamplifier gain that are particularly troublesome during long experiments. However, it does not change the absolute amplitude of J-modulated signal, so the signal-to-noise (SNR) ratio resulting from additive error sources such as thermal noise generally remains unchanged.

Most hydrocarbons contain a range of single-bond J-coupling constants. However, the pulse sequence of FIG. 3B acts as a perfect excitation pulse for one value of J (the one that satisfies the condition $\tau'=1/(2J)$). A simple vector analysis of the pulse sequence for arbitrary values of the precession angle $\theta=\pi J\tau'$ (i.e., for any value of the coupling constant), shows that the final magnetization produced by the cluster is given by $$\vec{M}_{coupled}=-(=(\sin^2\theta)\hat{y}+(\cos^2\theta)\hat{z};\ \vec{M}_{uncoupled}=\hat{z} \quad (4)$$

Figure 4A:
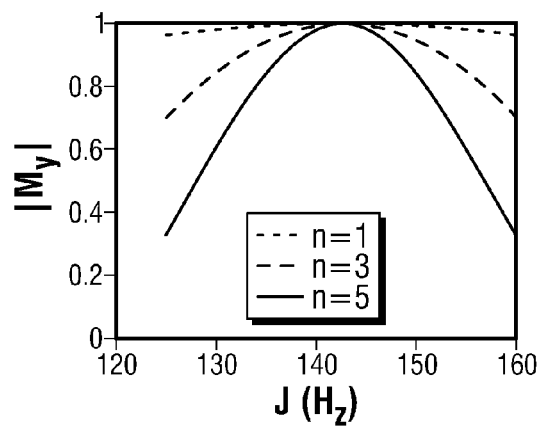
FIGS. 4A and 4B include two plots of J-filtering functions produced by the chemically-selecting J-editing pulse sequence of FIG. 3B for various values of time delay $\tau'$.
Figure 4B:
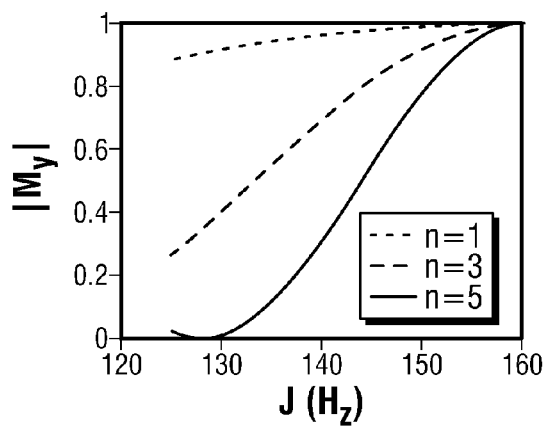

As expected, all the coupled magnetization ends up along the y-axis when $\theta=\pi/2$, i.e., $\tau'=1/(2J)$. In general, such perfect excitation is obtained whenever $\tau'=n/(2J)$, where n=1, 3, . . . . The uncoupled magnetization remains zero for other values of $\theta$, but the amount of coupled magnetization along the y-axis decreases. As a result, the amount of J-modulated signal also decreases. Hence the selective excitation pulse sequence used in FIG. 3B with a fixed value of $\tau'$ also acts as a "J-filter," preferentially selecting spins that satisfy the condition $\tau'=n/(2J)$ and suppressing the others. The value of $\tau'$ can therefore be varied to enhance or suppress the J-modulation produced by different chemical groups. FIGS. 4A and 4B show these filter functions for various values of n for two frequencies (J=142 Hz, and J=160 Hz).

FIGS. 4A and 4B show that the amount of frequency selectivity increases with n. For example, by setting $\tau'=3/(2\times 160\ Hz)=9.375$ ms, the J-modulated signal from single-bonded carbons (J≈125 Hz) may be suppressed while emphasizing that from double-bonded and aromatic carbons (J 160 Hz). This behavior can be useful for detecting double bonds or aromatic rings, because it removes the (usually much larger) background signal produced by single bonds. However, signal loss due to relaxation and diffusion also increases with the time delay $\tau'$, thus limiting the maximum useful value of n. In addition, in practice it is not possible to completely suppress the uncoupled magnetization primarily because of inaccurate flip angles of the RF pulses due to limited probe bandwidth and spatially inhomogeneous magnetic fields (both $B_0$ and $B_1$). For example, a tuned-and-matched probe with limited bandwidth BW produces RF pulses with finite rise and fall times $T_{tr}\sim 1/BW$. These transients reduce the effective length and flip angle of each RF pulse in the sequence. Their effects can be minimized by appropriately lengthening each pulse.

Those skilled in the art will appreciate that crude oils are often chemically analyzed using the "SARA" technique which uses a variety of analytical techniques, such as thin-layer chromatography and flame ionization, to separate oil samples into four main fractions based on their polarizability and polarity: Saturates, Aromatics, Resins, and Asphaltenes. Saturates (linear, branched, and cyclic aliphatic compounds) are non-polar, while Aromatics (mono- and poly-cyclic aromatic compounds) are slightly polar. Resins (heterocyclic compounds, acids, bases, phenols), and Asphaltenes (high-molecular-weight aggregates) are both polar, but only the former will dissolve in an excess of heptane or pentane. It is difficult to correlate these fractions with NMR spectra, because they measure properties of complete molecules and not their atomic structures.

Those skilled in the art will also appreciate that drilling muds or fluids are often separated into two basic types: water-based fluids (WBFs) and non-aqueous-based fluids (NABFs). Water forms the continuous phase in WBFs, while a liquid hydrocarbon mixture or other insoluble organic chemical forms the continuous phase in NABFs. NABFs are more expensive but are often used in difficult drilling situations to improve performance. NABFs, in turn, can be sub-divided into three types based on the chemical composition of the base fluid: oil-based fluids (OBFs), enhanced mineral oil-based fluids (EMOBFs), and synthetic based fluids (SBFs). OBFs, which are the least expensive, use diesel oil or normal mineral oil as the base. EMOBFs use an enhanced mineral oil as the base. The term "enhanced" refers to treatments that remove aromatic hydrocarbons (particularly polycyclic ones) SBFs use a synthesized, non-petroleum-origin liquid hydrocarbon base fluid to increase biodegradability.

The most common synthetic base fluids are hydrocarbons comprising olefins. An olefin is a cyclic or acyclic unsaturated chemical compound that includes at least one unconjugated carbon-carbon double bond. In turn, an aromatic is a chemical compound containing at least one conjugated ring of unsaturated carbon-carbon bonds. Olefins include include linear alpha olefins (LAOs), poly alpha olefins (PAOs), and internal olefins (IOs), as shown in FIG. 5. LAOs contain a terminal double bond, while PAOs and IOs contain an internal double bond. Typical LAO mixtures used in SBFs are $C_{14}C_{16}$ (a blend of $C_{14}H_{28}$ and $C_{16}C_{32}$) and $C_{16}C_{18}$. About 28% of LAO molecules typically contain branching, with most branches being methyl groups. PAOs used in SBFs have varying degrees of branching and carbon chain lengths, ranging from $C_8H_{16}$ to $C_{30}H_{60}$, with $C_{20}H_{40}$ being typical. More than 90% of PAO molecules contain branching. Commercial IOs have carbon chain lengths of 16 or 18 ($C_{16}C_{32}$ or $C_{18}C_{36}$), with more than 20% of the molecules containing branching. In today's market LAOs and IOs are usually preferred over PAOs. Other, less common, base fluids include esters, which are more biodegradable than olefins.

It should be noted that the base fluid usually represents only 30%-90% of the total volume of the complete mud, with the remainder consisting of water (which forms a brine-in-SBF emulsion), emulsifiers, wetting agents, thinners, weighting agents, and gelling agents.

Olefin-based SBFs contain more double bonds than natural hydrocarbons (crude oils). In addition, they generally do not contain aromatic hydrocarbons, unlike most crude oils. The absence of aromatics is largely responsible for the increased biodegradability of SBFs. In one aspect, these chemical differences make it possible to detect contamination of reservoir fluid samples with SBF drilling mud using NMR J-editing with frequency selectivity techniques. In another aspect, it is noted that while double bond signals produced by aromatic protons have similar values of J-coupling to double signals produced by olefins (160 Hz versus 150 Hz), the two are distinguishable using the J-editing with frequency selectivity techniques as previously described and as described in more detail hereinafter. Also, while a high SNR is desirable for J-editing techniques, and protons attached to double-bonded carbons typically contribute less than 10% of the J-coupled proton signal (corresponding to <0.1% of the total proton signal), according to yet another aspect, the SNR may be increased using reference scans as described hereinafter.

One source of noise relates to magnetic field fluctuations at 60 Hz and harmonics thereof which are ubiquitous because 60 Hz is a standard power line frequency. In one experiment, the pulse sequences of FIGS. 1 and 3B were used on a sample of an alkane (dodecane) to measure J-modulation in the time domain with spin echoes. The resulting measured J-modulation amplitudes were always lower than the theoretical value of 1.1%. One possible reason for this decrease is inaccurate flip angles of the RF pulses, caused both by errors in pulse lengths and variations in $B_1$ field strength within the sample. These errors accumulate as the number of encoding cycles increases, causing the modulation amplitude to also decrease with N. Smaller samples can be used to improve field homogeneity within the sample, thus reducing these effects. In addition, it was found that the modulation amplitude depended on $T_{E1}$, with maxima and minima occurring when $T_{E1}/2$ was an integer or half-integer multiple of 1/60 Hz, respectively. This behavior, which is shown in FIG. 6, suggests the presence of 60 Hz interference in the experiment. In FIG. 6, the J-modulation curve of dodecane is shown for various values of the initial echo period $T_{E1}$, with N=1 and $f_0$=60 Hz. J-modulation is observed at 125 Hz (indicating carbons with single bonds) as expected. However, as seen in FIG. 5, the amplitude is maximized for $T_{E1}=2/f_0$, and nearly disappears for $T_{E1}=3/f_0$.

Figure 7:
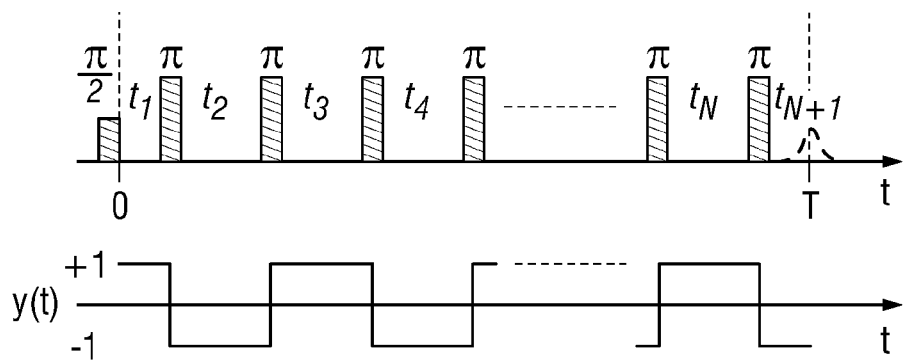
FIG. 7 is a spin echo sequence consisting of an excitation pulse and a train of N refocusing pulses, and a modulation function y(t).

Local variations in the magnetic field within the sample resulting from magnetic field fluctuations at 60 Hz and its harmonics create a time- and position-dependent resonance offset $\Delta\omega(\vec{r}, t)$ that contributes a term $\hbar \Delta\omega(\vec{r},t)I_z$ to the Hamiltonian during free precession, where $\hbar$ is Planck's constant divided by $2\pi$ and $I_z$ is the spin operator for z-magnetization. Spin-echo sequences are conveniently viewed in an interaction representation where each $\pi$ pulse rotates the Hamiltonian instead of the initial magnetization, creating a so-called "toggling frame Hamiltonian" $\tilde{H}$. In this representation, shown in FIG. 7, where a typical spin echo sequence consisting of an excitation pulse and a train of N refocusing pulses is shown, each $\pi$ pulse inverts the sign of the fluctuating term, resulting in $$\tilde{H}=\hbar \Delta\omega(\vec{r},t)y(t)I_z, \quad (5)$$

where the modulation function y(t) (also shown in FIG. 7) created by the pulses is defined as $$y(t) = \begin{cases} 1, & j \text{ is odd} \\ -1, & j \text{ is even} \end{cases} \quad (6)$$

Here $t_j$ is the set of free precession intervals between pulses, with j=1, 2, 3 . . . . In any spin-echo sequence the sum of even and odd delays are equal, making the average value of y(t) zero. This condition removes the effect of all static resonance offsets, i.e., the direct current (DC) component of $\Delta\omega(\vec{r},t)$. If only static offsets are present the "average Hamiltonian" $\overline{H}=\int \tilde{H}(t)dt=0$. However, in general, the effect of fluctuating resonance offsets is not removed. These components contribute a random phase shift $\varphi(T)$ after each interval T of free precession:

$$\varphi(T)=\int_0^T \Delta\omega(\vec{r},t)dt=\int_0^T\int_{-\infty}^{\infty} G(\vec{r},\omega)e^{-i\omega t}d\omega dt. \quad (7)$$

In equation (7), the fluctuation is decomposed into its frequency components $G(\vec{r},\omega)$. The explicit position dependence is dropped for simplicity. Consider a single frequency component $\hbar G(\omega)e^{-i\omega t}I_z$. It will create toggling frame and average Hamiltonians given by $$\tilde{H}=\hbar G(w)y(t)e^{-iwt}I_z$$

$$\overline{H}=\int \hbar G(w)y(t)e^{-iwt}I_z dt=\hbar G(w)\tilde{y}(w)I_z \quad (8)$$

The average Hamiltonian due to this frequency component is proportional to the amplitude of the modulation function $\tilde{y}(w)$ at that frequency, which in general is not zero. The result is an average frequency shift that depends on the phase of $G(\omega)$. Since this quantity will vary with time, the echo will acquire a random phase shift $\varphi$ with variance $\sigma_\varphi^2 \propto |G(w)|^2|\tilde{y}(w)|^2$. The quantity $|G(w)|^2$ is equivalent to the spectral density $J(\omega)$ in NMR relaxation theory, while $|\tilde{y}(w)|^2$ is the power spectral density of the modulation function created by the refocusing pulses. The latter acts as a filter, determining the sensitivity of the pulse sequence to field fluctuations at various frequencies.

Figure 8A:
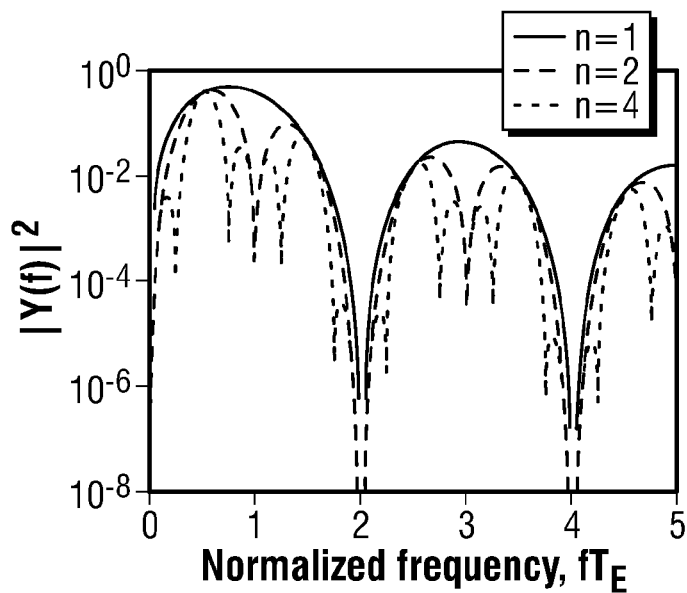
FIGS. 8A and 8B include calculated modulation functions for spin echo sequences with uniform spacing between refocusing pulses for various numbers of refocusing pulses.
Figure 8B:
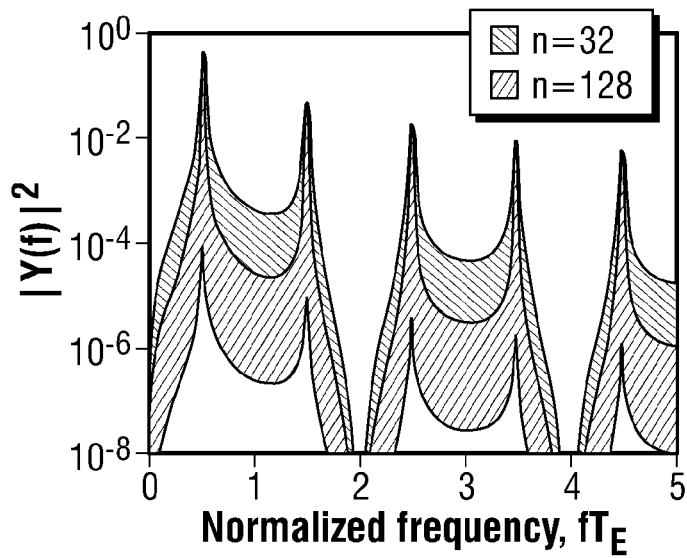

The filter function can be easily calculated for any multiple echo sequence. It is shown in FIGS. 8A and 8B for various values of N, which is the number of refocusing pulses. A uniform echo spacing $T_E$ has been assumed, which is the case for the J-editing sequence, both during encoding (when $T_E=T_{E1}$) and CPMG (when $T_E=T_{E2}$). The functions are always zero at DC (f=0), as expected for any spin echo sequence. However, the amount of suppression at low frequencies $<<1/T_E$ increases with N. Nulls also occur at frequencies that are even multiples of $1/T_E$ for all values of N. Thus, fluctuations at $2/T_E$, $4/T_E$, etc. are suppressed, and do not contribute any random phase to the final echo. On the other hand, for N=1 broad maxima occur around odd multiples of $1/T_E$, resulting in large contributions from field fluctuations at these frequencies. As N increases y(t) approaches a symmetric square wave of period $T_E$, so the maxima become progressively sharper and move to $f(n)=(n+1/2)/T_E$, where n=0, 1, 2 . . . .

FIGS. 8A and 8B suggest that 60 Hz fluctuations should have no effect on the J-editing sequence when $T_{E1}=2/(60 \text{ Hz})$ (where $\tilde{y}(w)=0$). They will have a non-zero effect when $T_{E1}>2/(60 \text{ Hz})$, and increase further when $T_{E1}=3/(60 \text{ Hz})$ (where $|\tilde{y}(w)|$ reaches a maximum). This prediction is correlated with the observed change of J-modulation amplitude with $T_{E1}$ shown in FIG. 6. This behavior may be understood more quantitatively by referring to the vector model shown in FIGS. 2A-2G. At the end of the echo cycle (position F), field fluctuations will cause both J-coupled vectors to rotate by the same random phase shift $\varphi$ as the overall echo. The real component of the resulting modulated signal is given by $$s(\theta + \phi) = \frac{1}{2}[\cos(\theta + \phi) + \cos(\theta - \phi)] = \cos(\theta)\cos(\phi). \quad (9)$$

Figure 9A:
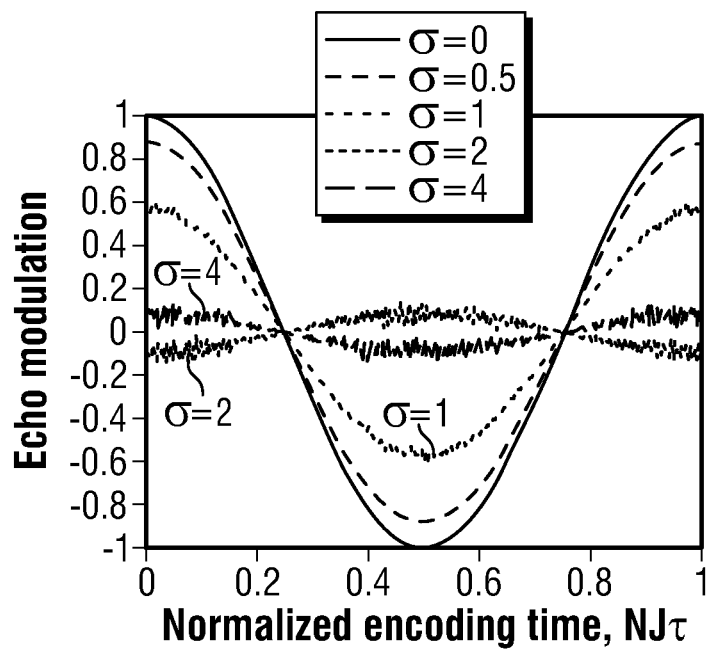
FIGS. 9A and 9B include calculated J-modulation functions for various amounts of random phase shift $\varphi$ in the echo, with FIG. 9A assuming a uniform distribution and FIG. 9B assuming a normal distribution.
Figure 9B:
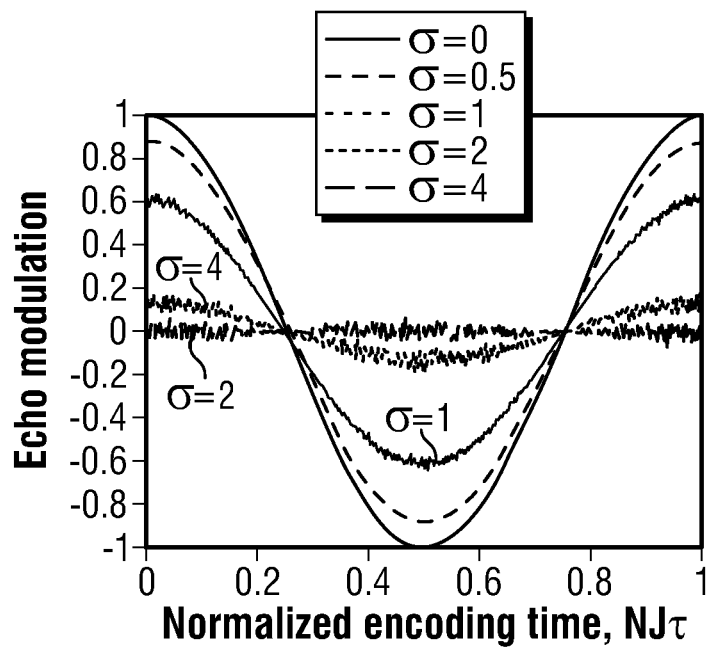

Thus, the random phase shift φ acts as a source of multiplicative noise on the J-modulation signal. The multiplicative nature of this error source means that it modulates the signal energy at the noise frequency, so the noise is not removed by signal averaging. Its effects are shown in FIGS. 9A and 9B for various values of the standard deviation $\sigma_\varphi \propto |G(w)\tilde{y}(w)|$. FIGS. 9A and 9B provide curves resulting from the averaging of one thousand realizations of $s(\tau,\varphi)$, and shows that the J-modulation amplitude decreases to zero as $\sigma_\varphi$ increases, both when φ is uniformly distributed (FIG. 9A) and when it is normally distributed (FIG. 9B). The modulation signal is not recovered by averaging, as expected for a multiplicative noise source. This behavior is in excellent agreement with the experimental results shown in FIG. 6.

An important advantage of the J-editing sequence is the ability to add together $N_E \gg 1$ spin echoes to improve SNR. However, this results in $T_2$-weighting of the different J-modulation components. Equation (3) must be modified to $$S(N\tau) = a_0 + \sum_{i=1}^{M}\left[a_i \cos(2\pi J_i N\tau) \sum_{j=1}^{N_E} e^{-jT_{E2}/T_{2,i}}\right]. \quad (10)$$

Here $T_{2,i}$ is the relaxation time of the i-th J-modulation component. Relaxation times in bulk liquids can be written as the sum of several components:

$$\frac{1}{T_{n,bulk}} = \frac{1}{T_{n,intra-dp}} + \frac{1}{T_{n,inter-dp}} + \frac{1}{T_{n,para}} + \frac{1}{T_{n,sr}}. \quad (11)$$

Here n=1 or 2 (referring to $T_1$ or $T_2$, respectively). The terms respectively refer to relaxation due to intra-molecular dipole-dipole interactions, inter-molecular dipole-dipole interactions, paramagnetic species, and spin rotation. For protons, the first two terms are dominated by proton-proton dipolar coupling. However the former is more sensitive to translational motion of molecules, while the latter is more sensitive to molecular rotations. This combination of intra- and inter-molecular contributions means that proton relaxation times depend not only on the location of the proton within a molecule, but also on the other components of a liquid mixture. Thus, in complex mixtures such as crude oils, the single number $T_{2,i}$ must be replaced by a distribution of values. This $T_2$ distribution (denoted by $f(T_2)$) can be found by one-dimensional Laplace inversion of a measured CPMG spin-echo decay $s(t)$. In the presence of diffusion, this process can be replaced by a two-dimensional inversion to obtain a two-dimensional D-$T_2$ distribution (denoted by $f(T_2,D)$). Such inversions solve a "Fredholm type" integral equation. This process is numerically ill-conditioned, but has been extensively studied.

The NMR signal can be written in terms of this distribution as an integral equation of the type $$s(t) \int [f(T_2,D) K_R(t,T_2) dT_2] K_D(t,D,T_E) dD, \quad (12)$$

where $K_R$ and $K_D$ are kernel functions that model echo decay due to relaxation and diffusion, respectively. These kernels depend on the pulse sequence and $(B_0,B_1)$ distribution within the sample. For example, for a CPMG sequence in a constant $B_0$ gradient g, $K_R = e^{-t/T_{2,eff}}$, where $T_2 < T_{2,eff} < T_1$ is the effective time constant for transverse relaxation, and $K_D = e^{-\gamma^2 g^2 D T_E^2 t/12}$ where $T_E$ is the echo spacing. The NMR signal $s(0)$ in the absence of relaxation and diffusion (when the values of both kernels is 1) can now be easily estimated:

$$s(0) = \int [f(T_2,D) dT_2] dD. \quad (13)$$

The signal $s(0)$ is proportional to the total number of spins in the active volume, e.g. the bulk porosity of the formation for well-logging applications. Similar kernel functions can be derived for the J-editing sequence, allowing for the correction of diffusion and relaxation effects. For this purpose, it is desirable to acquire and store individual echoes (including those generated during the J-editing periods) separately, instead of simply being added together.

For simplicity, it can be assumed that such corrections are not necessary. In other words, the assumption can be made that the relaxation time distributions $T_{2,i}$ are identical for all J-modulation components. In this case, their fractions in the summed echo signal are the same as the coefficients $a_i$, i.e., the fraction of protons present within each component. With this caveat in mind, time-domain measurements from experiments using the J-editing sequence are described where $T_{E1}$ was fixed to equal 2/(60 Hz) or 4/(60 Hz) to avoid attenuation of the J-modulation signal due to weak 60 Hz fluctuations in the magnetic field.

Figure 10A:
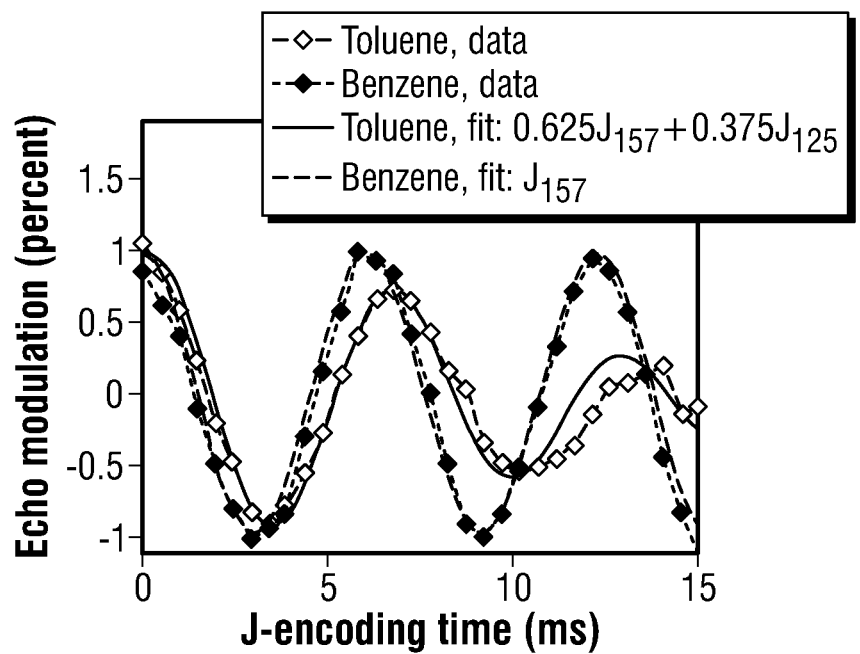
FIGS. 10A and 10B show measured J-modulation curves of benzene and toluene (FIG. 10A) and squalene (FIG. 10B) fit to models with one or two J-modulation components.
Figure 10B:
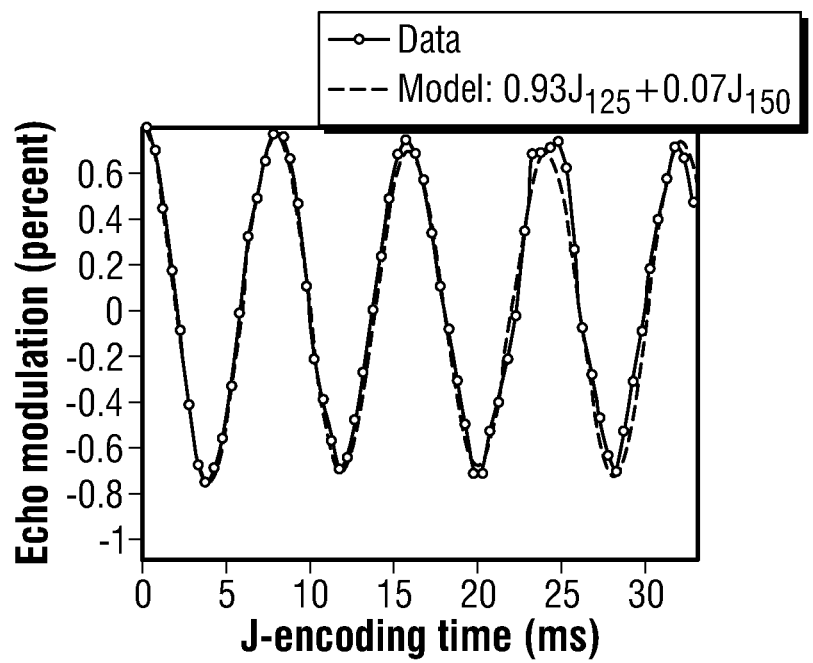

The following experiments were performed in a 9 T superconducting magnet, which resulted in $^1$H and $^{13}$C Larmor frequencies of 400 MHz and 100.5 MHz, respectively. FIGS. 10A and 10B show the measured J-modulation curves of benzene (an aromatic) and toluene (having an aromatic ring and a methyl group) (FIG. 10A), and the measured J-modulation curve of squalene ($C_{30}H_{50}$—an olefin derived from vegetable and shark liver oils) (FIG. 10B) using broadband RF pulses, e.g., pulses that have much larger bandwidths than the range of chemical shifts in the sample. In this specific case, it is assumed that the J-modulation components are excited and/or inverted in the same way. Fits to the expected modulation functions are also shown. The benzene curve fits to the J-coupling constant $J_{157}$. The toluene curve clearly shows the presence of the two different J-coupling constants in the molecule (3 methyl protons at 125 Hz, and 5 aromatic protons at 157 Hz), resulting in a good fit to the expected function $(5/8)J_{157}+(3/8)J_{125}$ where $J_f$ is shorthand notation for $\cos(2\pi fN\tau)$. In measuring the J-modulation curves of benzene and toluene, the experimental parameters included: 4 scans, N=1, $T_{E1}$=2/(60 Hz), $N_E$=128, and $T_{E2}$=3.2 ms. The squalene curve is well-fit by a function containing 7% modulation at 150 Hz, in reasonable agreement with the fact that 12% of protons in the molecule are attached to double-bonded carbon atoms. In measuring the J-modulation curve of squalene, the experimental parameters included: 16 scans, N=1, $T_{E1}$=4/(60 Hz), $N_E$=16, and $T_{E2}$=3.4 ms. Other parameters included $T_{90}$=4.3 μs and $T_{180}$=8.2 μs for the proton channel, and $T_{180}$=15.0 μs for the carbon channel.

The bandwidth of a rectangular inversion pulse is approximately $1/T_{180}$. The bandwidth of full-power carbon π pulses ($T_{180}$=15 μs) is about 663 ppm at a $^{13}$C Larmor frequency of 100.5 MHz. This value is much larger than the normal range of carbon chemical spectroscopy shifts of about 130 ppm discussed hereinafter, so it acts as a broadband pulse. Experiments were also performed with narrow-band, low-power carbon π pulses ($T_{180}$=112.5 μs). The bandwidth of these pulses was approximately 88 ppm, which is low enough to selectively invert carbon atoms that are single-bonded (14-40 ppm) or double-bonded/aromatic (114-140 ppm). In this way J-modulation due to one of these classes of protons can be selected while suppressing the other.

Figure 11A:
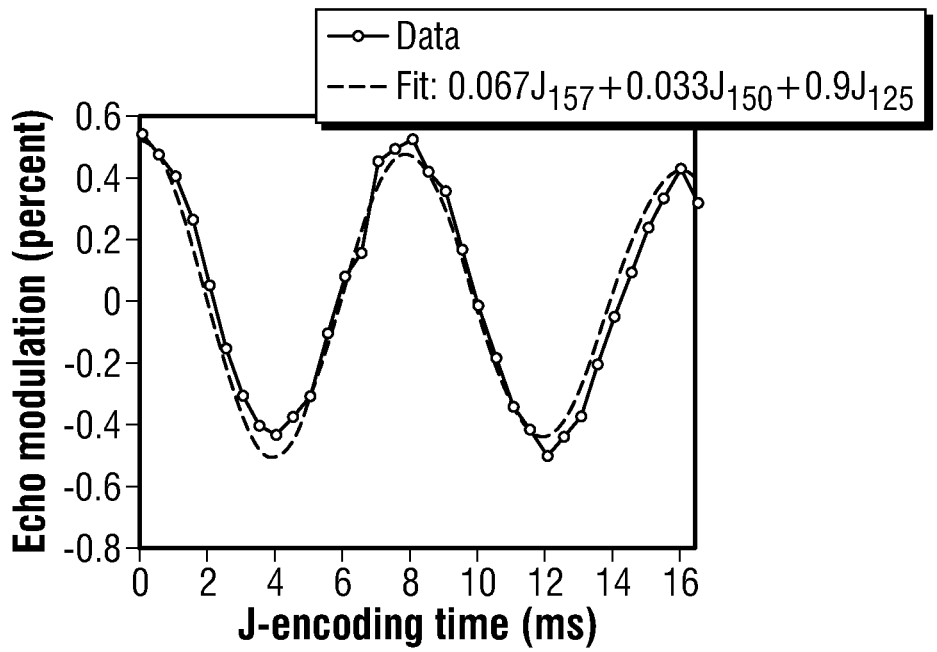
FIGS. 11A-11C show measured J-modulation curves of 1-decene with FIG. 11A resulting from using a broadband carbon inversion pulse, and FIGS. 11B and 11C resulting from using narrowband inversion pulses.
Figure 11B:
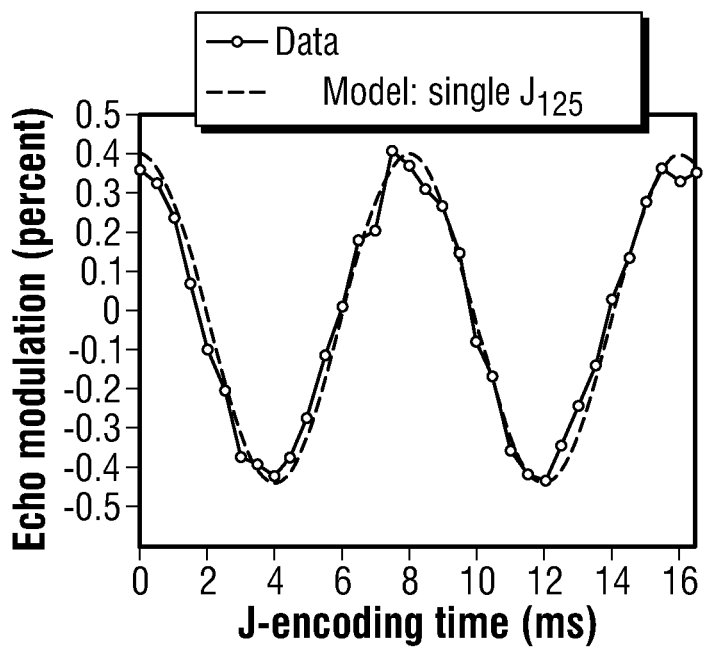
Figure 11C:
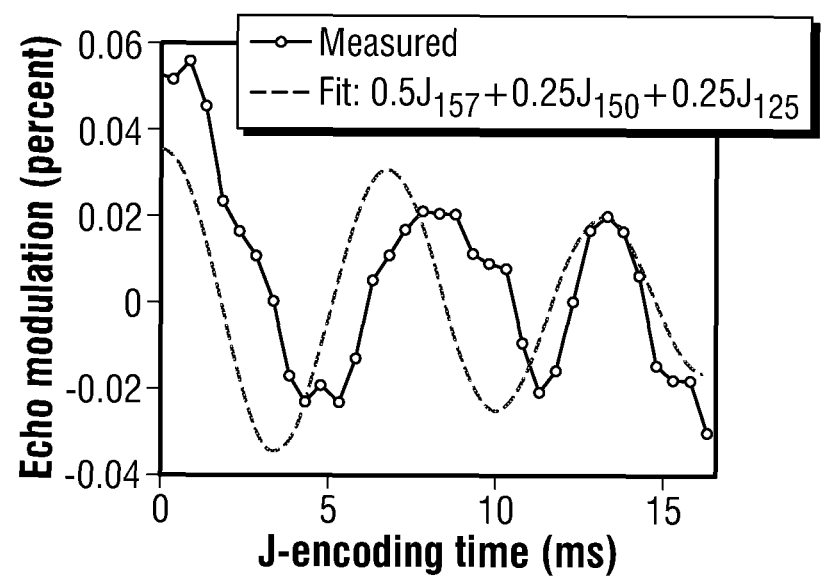

Some results featuring selective inversion are shown in FIGS. 11A-11C for 1-decene. As seen in FIG. 11A, the broadband carbon pulse results in a J-modulation curve with approximately 10% double-bond component (150 Hz and 157 Hz), in reasonable agreement with the expected value of 15%. As seen in FIG. 11B, this component disappears when a narrowband carbon inversion pulse centered in the single-bond region of the carbon spectrum (26 ppm) is used, and only the 125 Hz component remains. On the other hand, as seen in FIG. 11C, the normally dominant 125 Hz component nearly disappears when a narrowband carbon inversion pulse centered in the double-bond region of the carbon spectrum (125 ppm) is used. The remaining J-modulation is very small (less than 0.1% of the total signal) and hence suffers from poor SNR, but appears to be dominated by components at 150 Hz and 157 Hz, as expected.

Figure 12A:
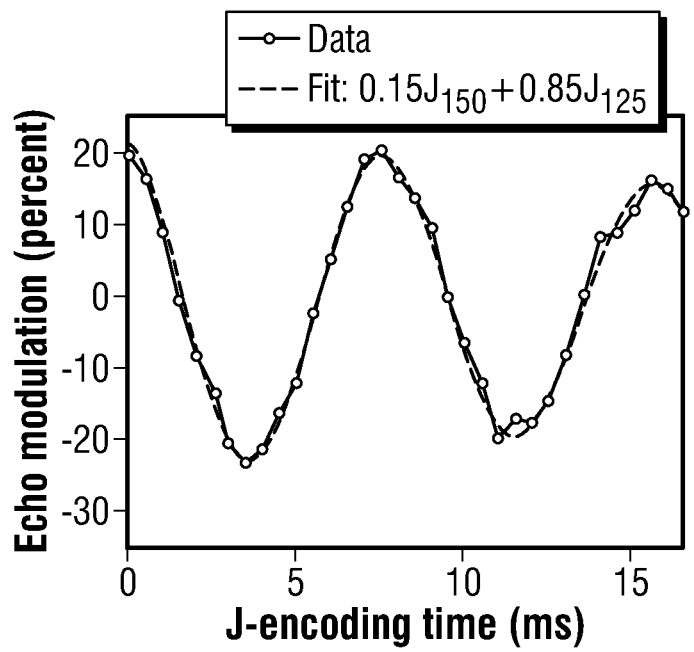
FIGS. 12A and 12B show measured J-modulation curves of squalene using the chemically-selective pulse sequence of FIG. 3B and with different time delays.
Figure 12B:
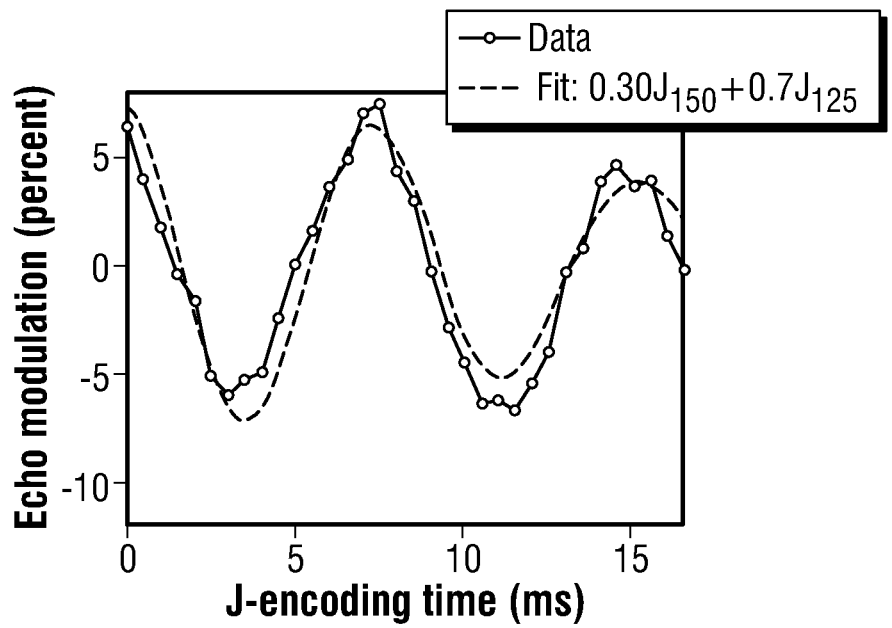

The effects of using a chemically selective pulse sequence of FIG. 3B to eliminate the unmodulated proton signal are shown in FIGS. 12A and 12B using squalene as an example. Experimental parameters resulting in the measurement curves of FIGS. 12A and 12B included 16 scans, N=1, $T_{E1}=2/(60$ Hz), $N_E=64$, $T_{E2}=3.4$ ms, $T_{45}=3.6$ µs. $T_{135}=6.5$ µs, and $T_{180}=8.2$ µs for the proton channel and $T_{180}=15.0$ µs for the carbon channel. FIG. 12A uses a delay of $\tau'=1/(142$ Hz)=3.5 ms. Note the change in vertical scale on this plot. The J-modulation amplitude exceeds 20%, implying that over 95% of the uncoupled proton signal has been suppressed by the chemically selective pulse sequence sequence. The J-modulated signal is well fit by a model with 15% double-bond component (at 150 Hz), in good agreement with the fact that 12% of protons in squalene are attached to double-bonded carbon atoms. FIG. 12B uses identical parameters, except for an increased delay of $\tau'=3/(142$ Hz)=10.5 ms. The J-modulation amplitude is smaller in this case, indicating more suppression of the dominant single-bond signal at 125 Hz. In addition, the best-fitting model for the J-modulated signal now contains 30% double-bond component. The fractional increase in this component is due to increased filtering of the single-bond signal at 125 Hz. This is also understood in conjunction with FIG. 4A. Thus, the delay of $\tau'=10.5$ ms corresponds to the n=3 curve of FIG. 4A, while the value $\tau'=3.5$ ms corresponds to the n=1 curve. The n=3 filter is sharper and removes more of the 125 Hz signal, resulting in fractional enhancement of the 150 Hz component. Thus, it is possible to emphasize or suppress various J-modulation components by varying the time delay $\tau'$ within the chemically selective pulse sequence.

According to one aspect, one issue with making measurements using J-editing sequences is the presence of temperature and gain drifts during long experiments. Thermal polarization (and hence signal amplitude) is proportional to $1/T_A$, the absolute sample temperature. Changes in sample temperature between scans with different values of the J-encoding time $\tau$ therefore cause signal amplitude changes that can be confused with the effects of J-modulation. In addition, the Larmor frequency strongly depends on magnet temperature. The bandwidth of the RF pulses is usually much larger than such Larmor frequency changes, unless very long experiments are being performed. As a result the signal amplitude is relatively constant with changes in magnet temperature, apart from second-order effects (such as the fact that signal amplitude is proportional to $B_0^2$). However, the resulting drifts in Larmor frequency often cause large changes in the absolute phases of the echoes between scans. This makes signal averaging difficult. To address these changes, each scan can be individually phase-corrected before averaging. A final source of error is temperature changes in the spectrometer electronics which may cause signal amplitude changes between scans that can be confused with J-modulation.

In order to overcome effects of temperature and gain drifts, in one embodiment, reference scans were run at frequent intervals. The reference scans were identical to the J-editing sequence, but with the $^{13}C$ pulse turned off. These scans provide the current unmodulated signal amplitude, thus allowing the change in amplitude due to J-modulation to be calculated more accurately.

The complete experiment was set up as a set of four nested loops, as follows: Inner loop—a four-part phase cycle (using either reference or normal scans); Second loop—run alternating reference and normal scans ($^{13}C$ pulse on, $^{13}C$ pulse off), and subtract the results of the two scans to get the J-modulation; Third loop—vary J-encoding period $\tau$ to get the J-modulation curve; and Outer loop—repeat the experiment to average the J-modulation curve and increase SNR.

In one embodiment, the effects of temperature and gain drifts are limited using reference scans to estimate the amount of J-modulation within the second loop, which typically completes in less than 30 seconds. The amount of drift within this short time span is usually negligible. It can be further reduced by using short $T_1$-recovery periods between scans (thus reducing the duration of the inner loop) and increasing the number of averages in the outer loop to recover SNR.

Figure 13A:
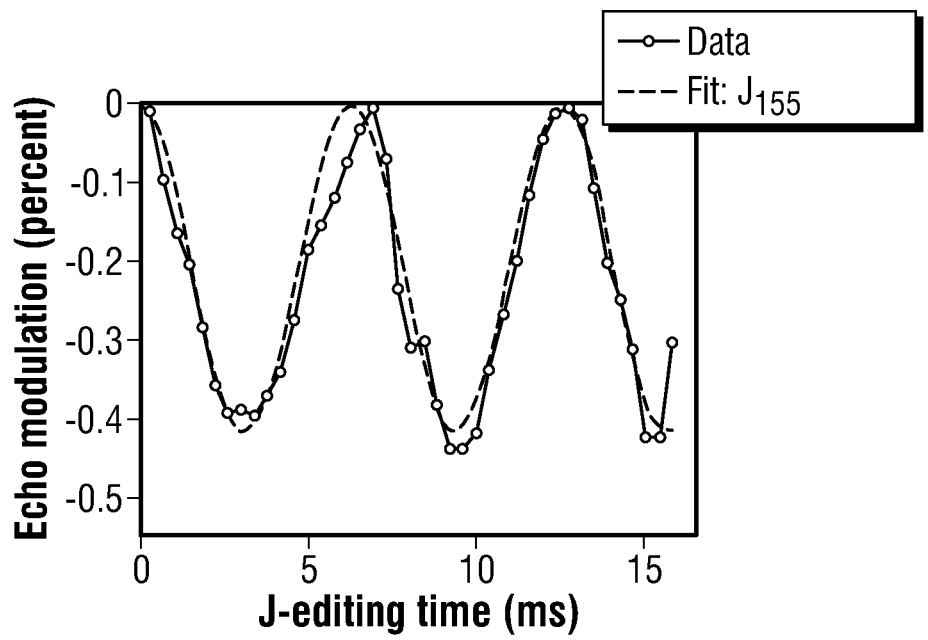
FIGS. 13A and 13B show measured J-modulation curves for benzene (FIG. 13A) and toluene (FIG. 13B) that fit to models with one or two J-coupling values respectively.
Figure 13B:
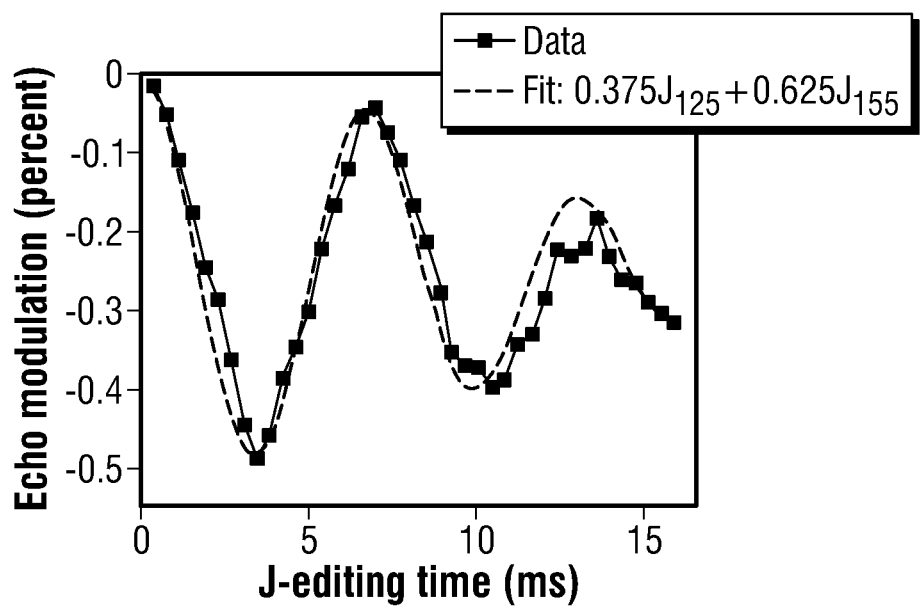

The following experiments were performed in a 0.5 T permanent magnet, which resulted in $^1H$ and $^{13}C$ Larmor frequencies of 21.8 MHz and 5.5 MHz, respectively. FIGS. 13A and 13B show measured J-modulation curves for benzene (FIG. 13A) and toluene (FIG. 13B) that fit to models with one or two J-coupling values respectively. The experimental parameters were 32 scans (benzene) or 64 scans (toluene), N=1, $T_{E1}=2/(60$ Hz), $N_E=600$, $T_{E2}=600$ µs, recycle delay=1.2 sec, $T_{90}=28.5$ Cis for the proton channel, and $T_{180}=80$ µs for the carbon channel. In both cases the fits result in the correct J-coupling values. In the case of toluene the relative proportions of aromatic (at 155 Hz) and methyl (at 125 Hz) components also match what is expected on the basis of molecular structure. However, the amplitude of the modulation is somewhat smaller than the theoretical value of 1.1% (the decreased amplitude having been similarly obtained in the other J-editing experiments). In the experiment from which FIGS. 13A and 13B were obtained, long samples (much longer than the RF coil of the NMR equipment) were used within standard 5 mm diameter NMR sample tubes in order to approximate a downhole flowline setup. This results in a fairly inhomogeneous $B_1$ across the sample, which may be responsible for at least some of the reduction in J-modulation amplitude.

Figure 14A:
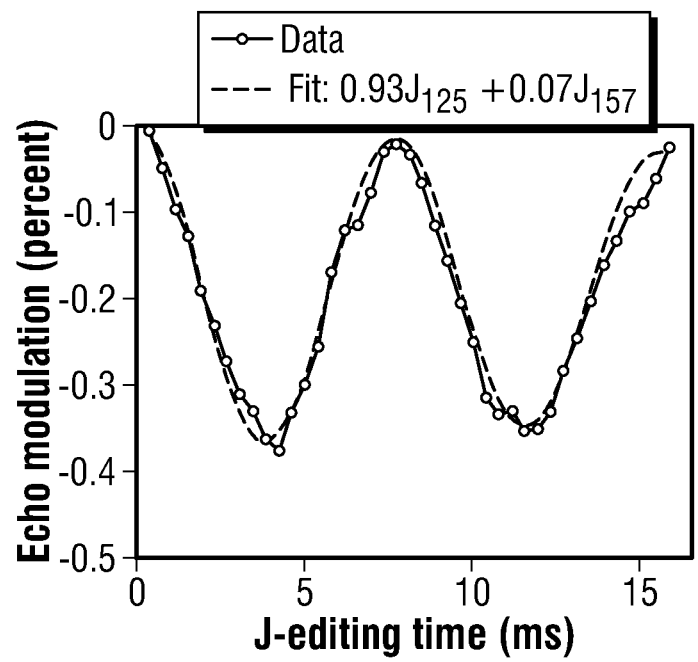
FIGS. 14A-14D show measured J-modulation curves for four samples, including crude Oil 8 (FIG. 14A), crude Oil 10 (FIG. 14B), an SBF base fluid (FIG. 14C), and squalene (FIG. 14D), and a fit to two-component models for each curve.
Figure 14B:
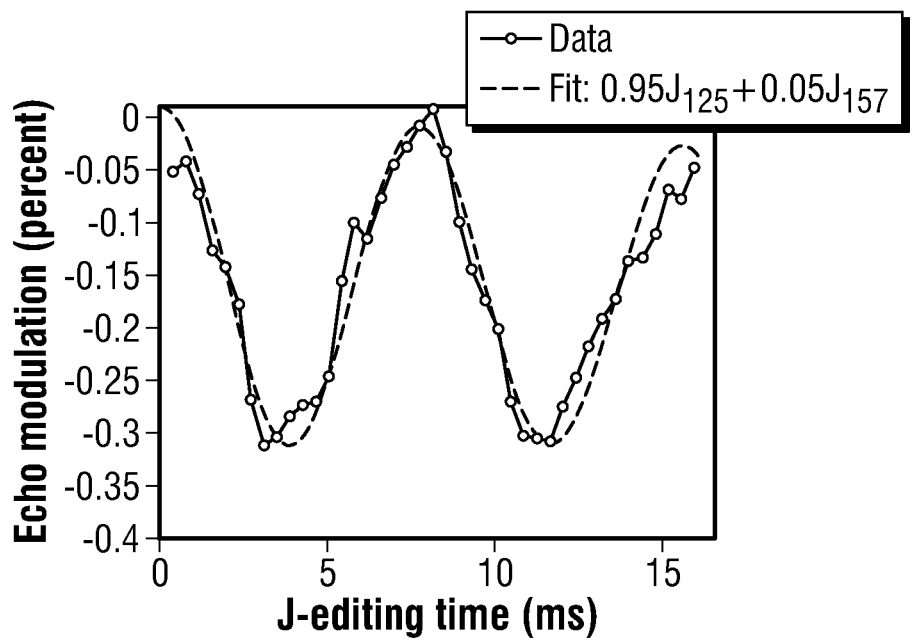
Figure 14C:
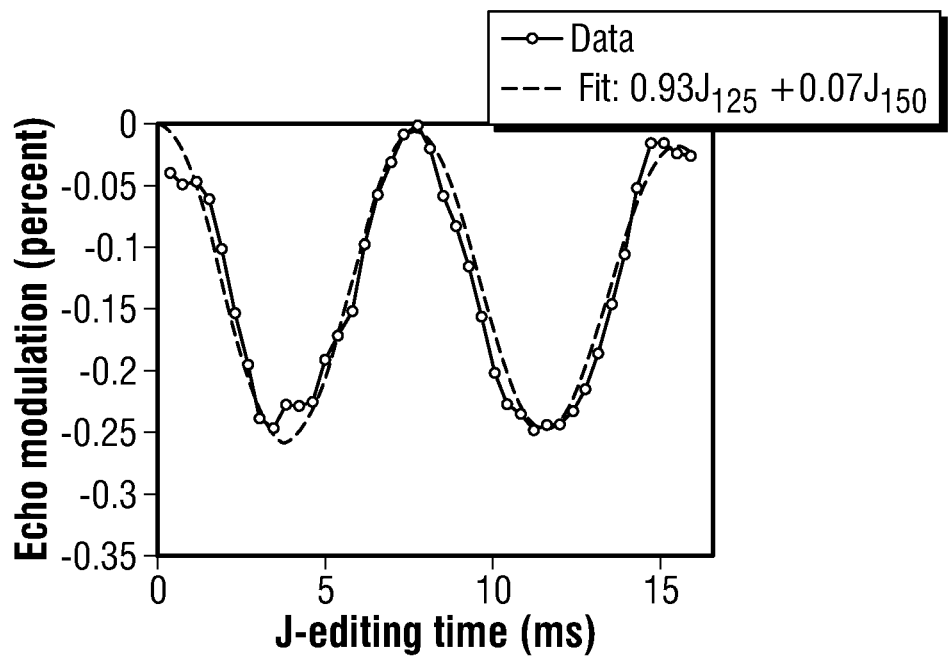
Figure 14D:
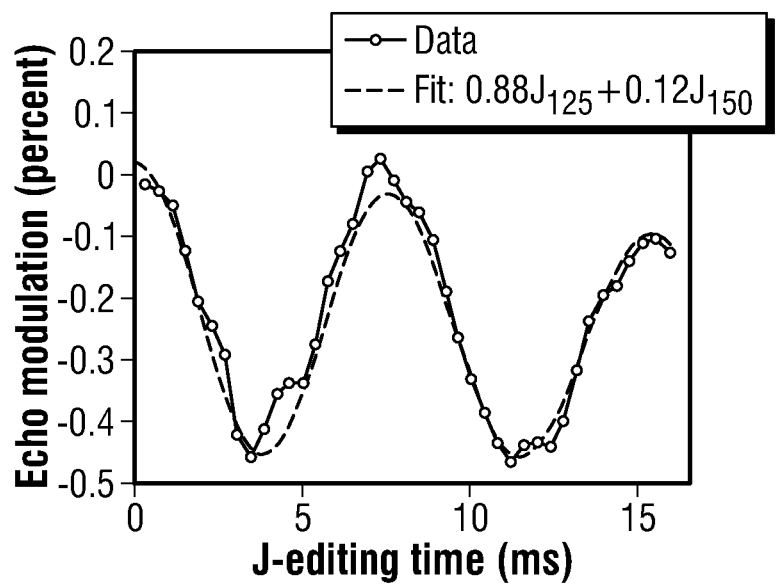

FIGS. 14A-14D shows measured J-modulation curves for four other samples: two crude oils named Oil 8 (FIG. 14A) and Oil 10 (FIG. 14B), an SBF base fluid (FIG. 14C), and squalene (FIG. 14D). The experimental parameters from which the curves were generated included 64 scans (except squalene) or 32 scans (squalene), N=1, $T_{E1}=2/(60$ Hz), $N_E=250$ (Oil 8) or 500 (Oil 10) or 600 (SBF) or 450 (squalene), $T_{E2}=600$ µs, recycle delay=0.85 sec (Oil 8) or 1.3 sec (Oil 10) or 1.24 sec (SBF and squalene), $T_{90}=28.5$ is for the proton channel, and $T_{180}=80$ is for the carbon channel. Each curve was fitted to a two-component model, consisting of J-modulation components at 125 Hz and either 150 Hz (for the olefins—SBF and squalene) or 157 Hz (for the crude oils). The total modulation amplitude varies somewhat between samples, and should also be treated as a fitting parameter. All these samples were also analyzed spectroscopically using NMR spectroscopy techniques described in co-owned U.S. patent application Ser. No. 14/067,475 filed on Oct. 30, 2013, which is hereby incorporated by reference herein in its entirety) and the fraction of non-saturated protons in the sample (measured using spectroscopy) is in reasonable agreement with the fraction of J-modulation between 150-157 Hz (measured by fitting the J-editing data) for a variety of samples, as shown in Table 2 below.

TABLE 2

| Compound | $^1$H non-saturates, % (9 T superconducting magnet, spectroscopy) | J-modulation, component at 150-157 Hz (0.5 T magnet, J-editing) |
|---|---|---|
| Benzene | 100 | 100 |
| Toluene | 62.5 | 62.5 |
| Squalene | 11.6 | 12.0 |
| Oil 8 | 5.1 | 7.0 |
| Oil 10 | 3.3 | 5.0 |
| SBF base | 5.6 | 7.0 |

This result confirms that time-domain J-editing measurements can be used to reliably infer the fraction of protons attached to double-bonded carbon atoms in hydrocarbon mixtures, whether located in aromatic rings, such as in benzene, toluene, Oil 8 and Oil 10, or located in olefins, such as in squalene and SBF. The fraction of protons attached to double-bonded carbon atoms can be used to determine characteristics of a hydrocarbon sample. For example, the fraction of protons attached to double-bonded carbon atoms in olefins can be used to determine a concentration of SBF contamination within a hydrocarbon sample (e.g., through knowledge or an estimate of olefinic weight percentage in the SBM). The concentration of SBM contamination in a hydrocarbon sample is an amount of SBM in relation to some or all other chemical components within the hydrocarbon sample. The concentration of SBM contamination can be a fraction or a percent, such as a weight percentage, a molar percentage, and/or a volume percentage. Furthermore, the concentration of SBM contamination in the hydrocarbon sample may be (i) a relative amount of some or all components of the SBM within the hydrocarbon sample, (ii) a relative amount of one or more olefins of the SBM within the hydrocarbon sample, (iii) and/or a relative amount of one or more nuclei of olefins within the hydrocarbon sample (e.g., a hydrogen weight percentage of the olefins).

In one aspect, J-editing techniques may be used in conjunction with NMR spectroscopy techniques. In one embodiment, NMR spectroscopy techniques (either or both of $^1$H and $^{13}$C) may be used to confirm the findings of the J-editing techniques regarding the presence or lack thereof of olefins in an oil sample. Where J-editing techniques are used to find a fraction of protons in the sample associated with olefins, the NMR spectroscopy techniques may be used to confirm the same. In another embodiment, J-editing techniques may be used to confirm the determination of the NMR spectroscopy techniques (either or both of $^1$H and $^{13}$C) finding the presence or lack thereof of olefins in an oil sample. Where NMR spectroscopy techniques are used to find a fraction of the sample associated with olefins, the J-editing techniques may be used to confirm the same. In another embodiment, NMR spectroscopy techniques (either or both of $^1$H and $^{13}$C) may be used to confirm the determination of the J-editing techniques of the presence of at least one of aromatics and aliphatics in an oil sample. Where J-editing techniques are used to find a fraction of protons in the sample associated with aromatics and/or aliphatics in the oil sample, the NMR spectroscopy techniques may be used to confirm the same. In another embodiment, J-editing techniques may be used to confirm the determination of the NMR spectroscopy techniques (either or both of $^1$H and $^{13}$C) of the presence of at least one of aromatics and aliphatics in an oil sample. Where NMR spectroscopy techniques are used to find a fraction of the sample associated with aromatics and/or aliphatics, the J-editing techniques may be used to confirm the same.

The previous experiments were performed in relatively homogeneous static magnetic fields. In such fields, the range of Larmor frequencies $\Delta\omega_0 = \gamma(\Delta B_0)$ is smaller than the RF nutation frequency $\omega$, so RF pulses uniformly excite the entire sample. Such conditions are not possible in NMR well-logging, in which the magnetic fields are weak and grossly inhomogeneous. We now describe techniques for performing J-editing experiments in such inhomogeneous "fringe" or "ex-situ" fields. According to one aspect, the semi-classical vector model is widely used for simulating the dynamics of non-interacting spin-1/2 particles such as protons. It can be easily extended to inhomogeneous magnetic fields by dividing the simulation region into small regions with constant $B_0$ and $B_1$ (known as isochromats), simulating the evolution of each isochromat independently, and adding the results. In one embodiment, a similar approach is used for simulating a J-coupled two-spin system in an inhomogeneous magnetic field. Instead of the vector model, a more general product operator formalism was used. The Hamiltonian for each isochromat in the system was written in a doubly-rotating frame, as follows:

$$H_{fp} = \Delta\omega_1 I_{z1} + \Delta\omega_2 I_{z2} + 2\pi J I_{z1} I_{z2}$$

$$H_{tot} = H_{fp} + \omega_{1,i}[I_{xi}\cos(\varphi) + I_{yi}\sin(\varphi)], \quad (14)$$

where $H_{fp}$ is its value during free precession, $H_{tot}$ is its value during an RF pulse of phase $\varphi$ on channel i, and $\Delta\omega_1$ and $\Delta\omega_2$ are the resonant frequency offsets of the two spins. In addition, $I_{x1}$, $I_{x2}$, etc. denote product operators (represented as 4×4 matrices) formed from the single-spin operators $I$, $I_x$, $I_y$, and $I_z$. The evolution of the density matrix $\rho$ was calculated in MATLAB (a trademark of The Mathworks, Inc. of Natick, Mass.) by using its expm function, i.e., by direct matrix exponentiation:

$$\rho(t+T) = e^{-iH_{tot}T}\rho(t)e^{iH_{tot}T}, \quad (15)$$

where $H_{tot}$ remains constant during the time period T, which can be an interval of free precession or an RF pulse. The observed signal on the i-th channel from each isochromat is given by $$s_i(t) = Tr(\rho(t)I_{xi}). \quad (16)$$

Figure 15A:
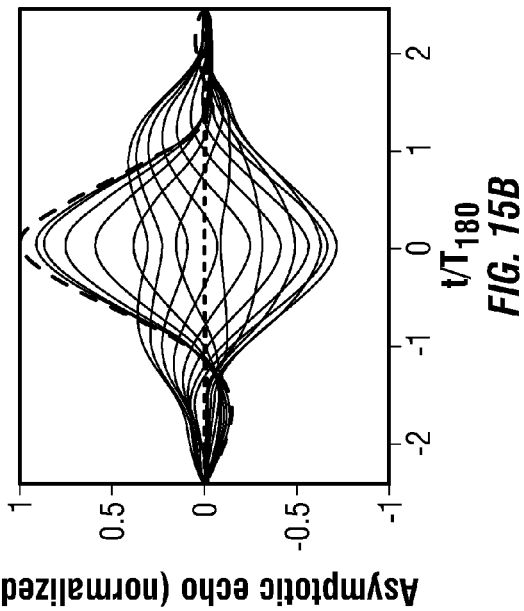
FIGS. 15A-15D show simulated J-modulated echoes for a J-editing sequence where J=125 Hz.
Figure 15B:
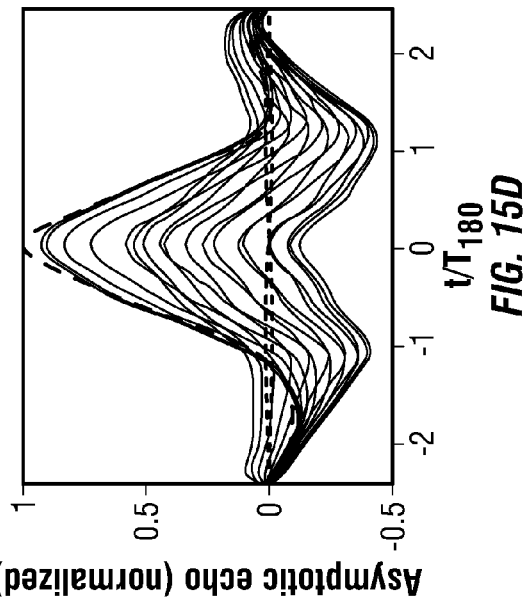
Figure 15C:
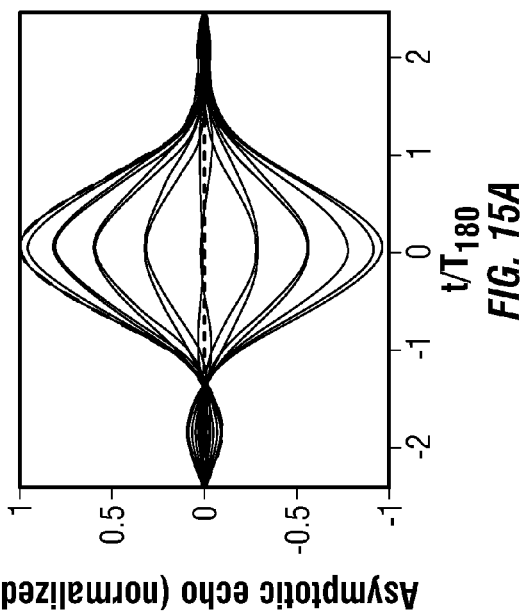
Figure 15D:
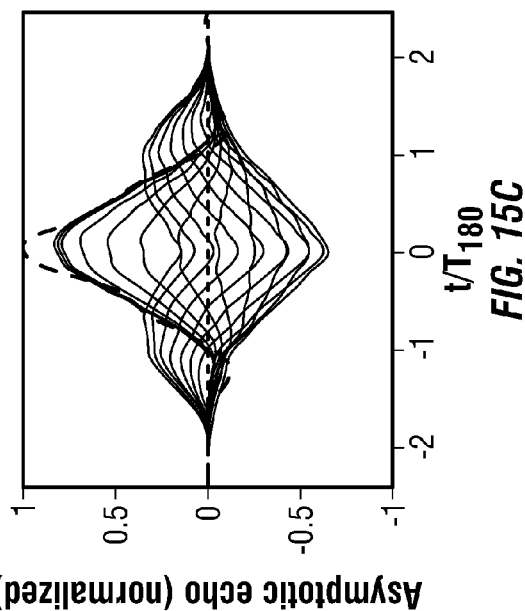
Figure 16A:
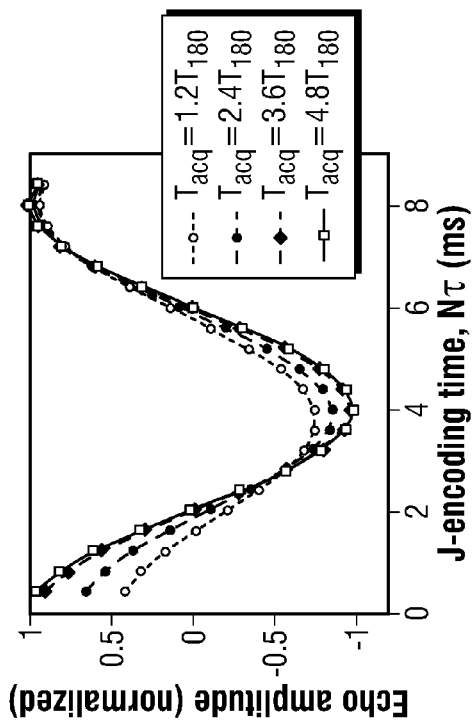
FIGS. 16A-16D show simulated J-modulation curves as a function of the J-encoding time $\tau'$ with various values of the number of J-encoding cycles N, the number of CPMG refocusing cycles $N_E$, and the acquisition window length $T_{acq}$.
Figure 16B:
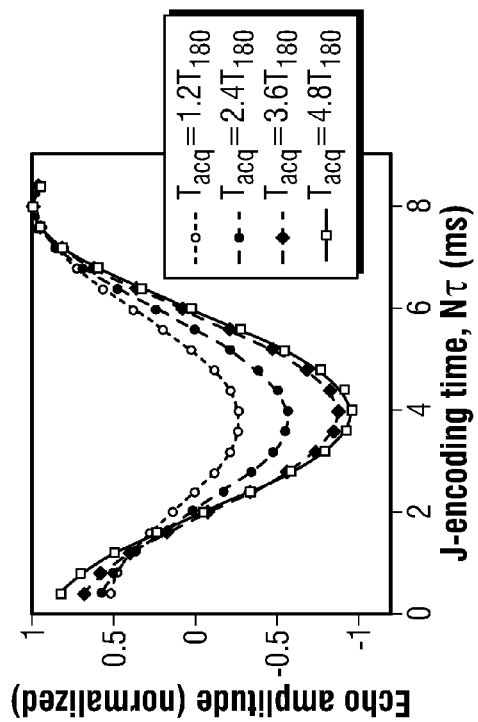
Figure 16C:
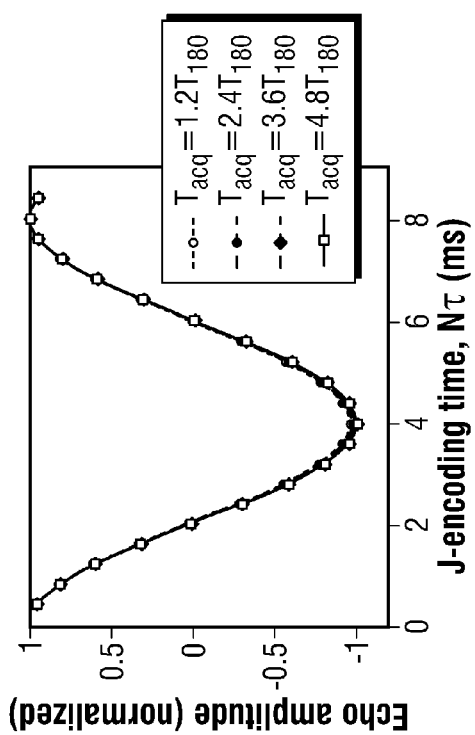
Figure 16D:
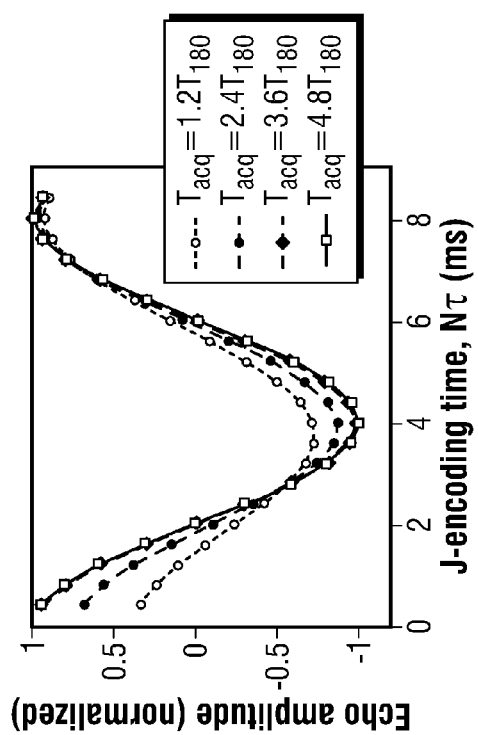

The total signal is obtained by adding the signals from isochromats in the sample. A uniform distribution of resonant frequency offsets across the isochromats (corresponding to a constant $B_0$ gradient, which is denoted by $g_z$) and no $B_1$ inhomogeneity were generally assumed. This is a good approximation for many fringe field systems, such as NMR well-logging tools. It should be noted that direct matrix exponentiation is computationally intensive, and other methods are often used for evolving the density matrix. FIGS. 15A-15D show simulated J-modulated echoes for the J-editing sequence assuming a constant $B_0$ gradient and uniform $B_1$ field. Plots are shown for J=125 Hz for various values of $\tau$ (the J-encoding time), N (the number of J-encoding cycles), $N_E$ (the number of CPMG refocusing cycles), and $T_{acq}$ (the length of the signal acquisition window). FIGS. 15A, 15B, 15C, and 15D use N=1, 2, 2, and 4 respectively, while keeping $N_E$ fixed at 2, except for the FIG. 15C, where $N_E$ was 0 (i.e., no CPMG present). All other parameters such as $T_{E2}$ were kept constant across simulations. Thus, FIGS. 15A-15D show the asymptotic CPMG echo shape as a function of the number of J-editing cycles with the dashed curves in each plot representing the echo shape with no J-modulation; i.e., with the $^{13}$C channel off. It is seen that for N=1, the echo shape is independent of τ to within a constant scaling factor. This is because there is just one coherence pathway (the direct echo) that can refocus the magnetization after a single J-editing cycle. As a result, the relative amplitudes of the echo integrals, and hence the shape of the J-modulation curve, should be invariant with $T_{acq}$. This expectation is confirmed in FIGS. 16A-16D where simulated J-modulation curves are shown for the J-editing sequence assuming a constant $B_0$ gradient and uniform $B_1$ field. In FIGS. 16A-16D, plots are shown as a function of τ for J=125 Hz with various values of N, $N_E$, and $T_{acq}$, with FIG. 16A representing N=1 and $N_E$=2, FIG. 16B representing N=2 and $N_E$=2, FIG. 16C representing N=2 and $N_E$=0, and FIG. 16D representing N=4 and $N_E$=2. In this specific example, all other parameters, such as $T_{E2}$ were kept constant across simulations.

FIG. 16A shows that the simulated J-modulation curves for N=1 are indeed invariant with $T_{acq}$. However, FIGS. 15A-15D show that the echo shape changes with r whenever N>1. Thus, according to one embodiment, the entire echo shape is acquired in order to obtain more accurate relative echo amplitudes and avoid distortion of the J-modulation curve. In other embodiments, the entire echo shape may not be acquired and used. This situation arises because now there are multiple coherence pathways (the direct echo and various stimulated echoes) that can refocus the magnetization after the J-editing cycles. The Fourier transform $S(\Delta\omega, \tau)$ of the time-domain echo $s(t,\tau)$ is given by $$S(\Delta\omega,\tau')=\int_{-\infty}^{\infty}s(t,\tau)e^{j\Delta\omega t}dt \quad (17)$$

If the integration window $[-T_{acq}, T_{acq}]$ covers the entire echo, the echo integral $s(\pi)$ is given by $$s(\tau)=\int_{-T_{acq}/2}^{-T_{acq}}s(t,\tau)dt \approx \int_{-\infty}^{\infty}s(t,\tau)dt=S(0,\tau) \quad (18)$$

Thus, if the entire echo shape is integrated, the echo integral $s(\pi)$ becomes equal to that of the on-resonance component (at $\Delta\omega$=0), which only has contributions from the direct echo pathway. In this case, the true J-modulation curve (the same as when N=1) is obtained with no off-resonant effects. However, for smaller values of $T_{acq}$ this condition is no longer satisfied, and some distortion of the resultant J-modulation curve can be expected. This expectation is confirmed in FIGS. 16A-16D. FIGS. 16B, 16C, and 16D show that the simulated J-modulation curves depend on $T_{acq}$, and approach the true curve when $T_{acq} >> T_{180}$. However, as $T_{acq}$ increases the minimum usable echo spacing $T_{E2}$ also increases, which reduces SNR. Fundamentally, this reduction in SNR arises because, for large values of $T_{acq}$, only the on-resonance component of the echo remains after integration.

FIGS. 15A-15D also show that the width of the echoes in the time domain increases with N. This means that the refocusing bandwidth decreases, i.e., the pulse sequence refocuses a smaller range of offset frequencies. As a result, longer values of $T_{acq}$ can be used to acquire the entire echo shape, causing SNR to decrease with N.

While the effects of J-editing cycles on the echo have been discussed above, the effects due to the CPMG pulse train have not been discussed because the refocusing bandwidth of the CPMG is likely to be significantly larger than that of the J-editing cycles. FIGS. 15C and 16C consider the case when no CPMG refocusing pulses are used ($N_E$=0) after two J-editing cycles (N=2). The bottom left plots can be compared with the corresponding plots on the top right of these figures, which use identical sequence parameters except for the addition of CPMG refocusing pulses at the end ($N_E$=2). The two sets of echo shapes and J-modulation curves are very similar, with the CPMG only producing a small increase in overall echo widths. This fact confirms the expectation that the CPMG pulse train should have little effect on echo shapes.

Figure 17:
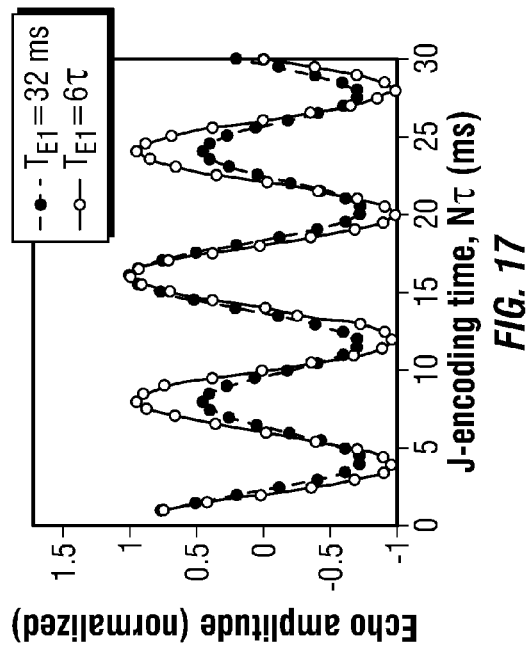
FIG. 17 shows simulated J-modulation curves for a J-editing sequence with a relatively short acquisition window length.

According to one aspect, it was determined that for N=2, the ideal J-modulation curve is restored for short acquisition times if the echo period during the J-editing cycles is varied as $T_{E1}$=6τ instead of keeping it fixed. FIG. 17, which shows simulated J-modulation curves for the J-editing sequence shows this effect for a relatively short acquisition window length ($T_{acq}$=1.2×$T_{180}$). In FIG. 17, the J-editing sequence assumes a constant $B_0$ gradient and a uniform $B_1$, and plots are shown for J=125 Hz using two J-encoding cycles (N=2) and five CPMG refocusing cycles ($N_E$=5) with the stated relatively short acquisition window length. The period of each encoding cycle was either kept fixed at $T_{E1}$=32 ms, or varied with the encoding time τ as $T_E$=6τ. The resultant J-modulation curve is significantly distorted when $T_{E1}$ is kept fixed with τ, as in the previous simulations. However, the true curve is recovered when $T_{E1} \approx 6\tau$.

Figure 18A:
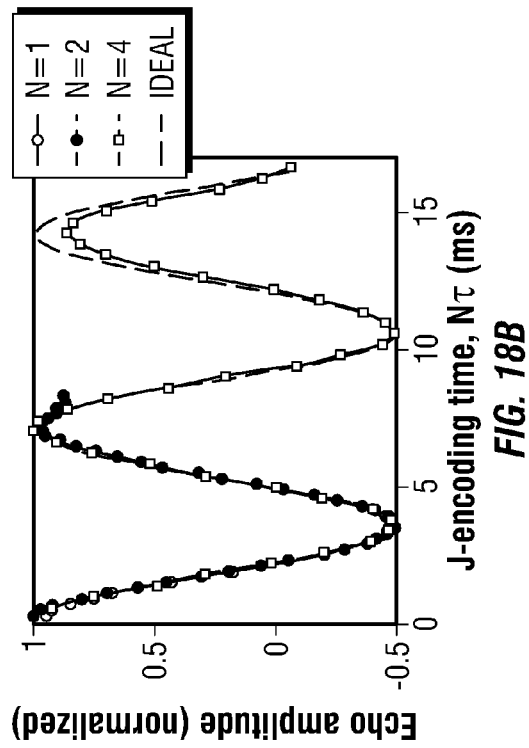
FIGS. 18A and 18B show J-modulation curves of methanol for various values of N.
Figure 18B:
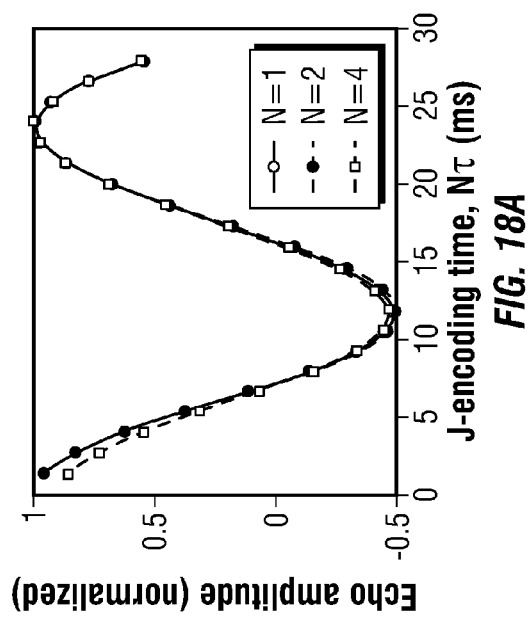

The following experiments were performed in the fringe field of a 2 T permanent magnet, which resulted in $^1$H and $^{13}$C Larmor frequencies of 1.545 MHz and 388.5 kHz, respectively. Turning to FIGS. 18A and 18B, plots are shown of J-modulation curves of methanol for various values of N. FIG. 18A shows simulated J-modulation curves for methanol (J=141 Hz) for N=1, 2, and 4 editing cycles, while the right-hand plot shows measured J-modulation curves for a $^{13}$C-enriched (99%) methanol sample (volume=5 ml) in the fringe field. Results were normalized to the unmodulated echo amplitude obtained with the $^{13}$C pulse(s) off. Experimental parameters included $f_H$=1.545 MHz, $f_C$=388.5 kHz, $g_z$=11.5 G/cm, $N_E$=500, $T_{E1}$=8.5 ms, $T_{E2}$=400 is, $T_{90}$=15 μs, $T_{acq}$=256 μs, and $N_{avg}$=4. In methanol, only the 3 methyl protons in the molecule are J-coupled to the carbon atom. Thus the expected modulation function is of the form a+b cos(2πJNτ'), where the offset b comes from the unmodulated hydroxyl proton and J=141 Hz is the tabulated value for methanol. In the ideal case, with complete J-modulation and identical T and $T_2$ for all protons, a=0.25 and b=0.75. In the experiment used to obtain FIG. 18B, a long acquisition interval ($T_{acq} \approx 8T_{180}$) was used, which eliminated distortion of the measured J-modulation curves when N>1. The resultant curves are in excellent agreement with simulations. The curves also fit the expected (ideal) modulation function 0.75+0.75 cos(2π141Nτ) very well, indicating that the methyl and hydroxyl protons have similar values of $T_1$ and $T_2$. However, a small decrease in modulation amplitude is noticeable at long encoding times for N=4. This effect may be due to pulse length calibration errors.

Figure 19A:
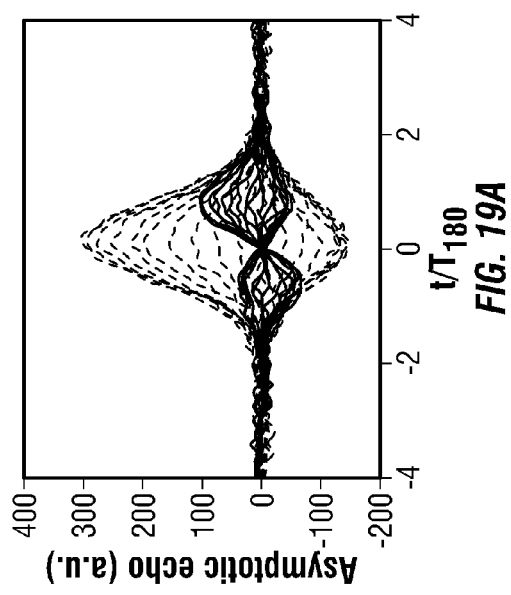
FIGS. 19A-19C show measured asymptotic echo shapes produced by a J-editing sequence for various values of N.
Figure 19C:
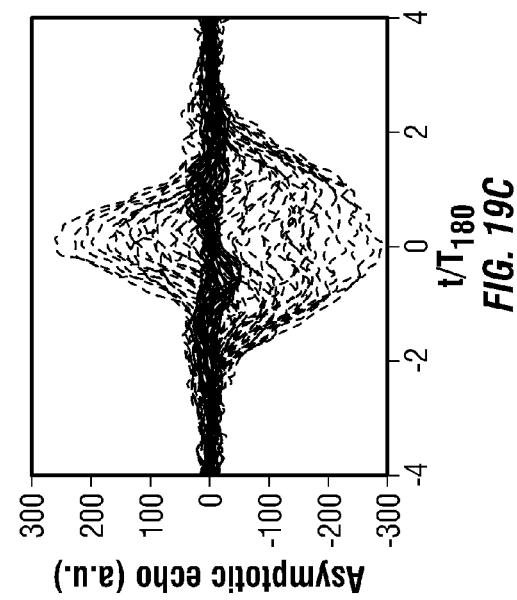
Figure 19B:
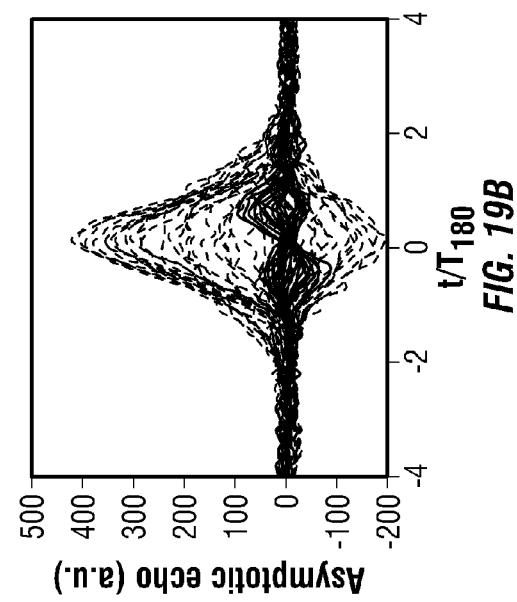

FIGS. 19A-19C show measured asymptotic echo shapes produced by the J-editing sequence for various values of N, which is the number of J-editing cycles. The same $^{13}$C-enriched methanol sample and the same experimental parameters used in the experiment of FIGS. 18A and 18B were used for this experiment. FIG. 19A corresponds to N=1, while FIGS. 19B and 19C correspond to N=2 and N=3, respectively. The curves within each plot correspond to various values of τ, the encoding time. The results are in good agreement with the simulated echo shapes shown in FIGS. 15A-15D. In particular, both simulated and measured echo shapes are invariant with the encoding time $\tau$ when N=1, but vary considerably with $\tau$ when N>1.

Figure 20:
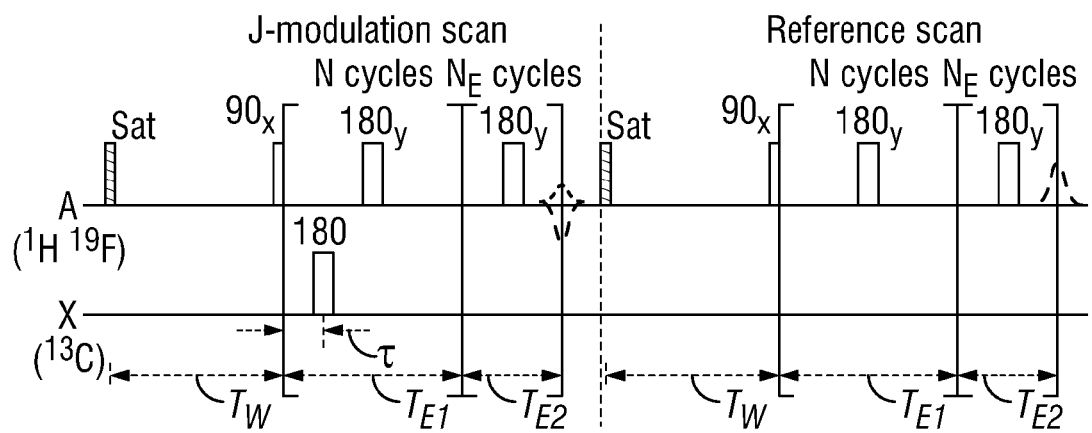
FIG. 20 shows a pulse sequence with an interleaved J-editing sequence consisting of a normal scan and a reference scan.

In one embodiment J-coupling in samples with natural abundance of $^{13}C$ (1.1%) was measured. These measurements were complicated by temperature drifts in the sample and receiver electronics. In order to avoid this problem, reference scans ($^{13}C$ pulses off) were incorporated between normal scans ($^{13}C$ pulses on), substantially as previously described. However, in this case, the order of the second and inner loops were reversed so that a pair of normal and reference scans was run as the inner loop, and phase cycling was run as the second loop. These pulse sequence for these scans are shown in FIG. 20 with an interleaved J-editing sequence consisting of a normal and a reference scan. Each scan begins with a saturation pulse (labeled "Sat"), followed by a polarization interval $T_w$. Initial saturation pulses are used to ensure identical amounts of polarization before each scan, thus eliminating the need for dummy scans. In addition, the phase of the excitation pulse is reversed during the reference scan, which inverts the unmodulated signal. As a result only the modulated signal remains after the echoes produced by both scans are added.

Figure 21:
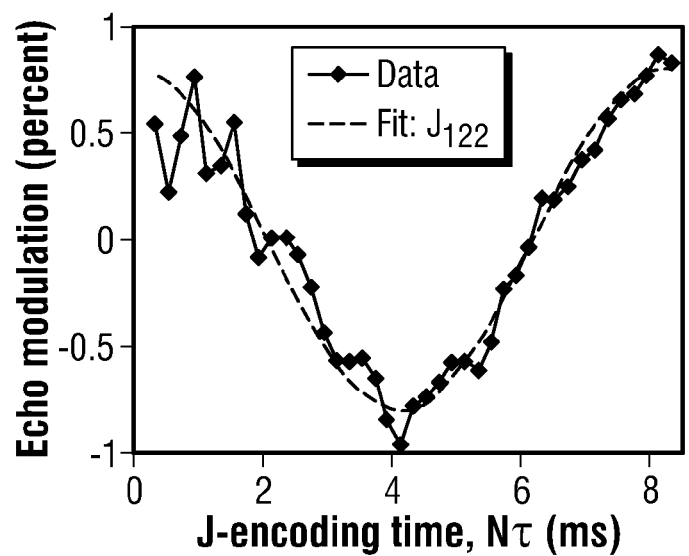
FIG. 21 shows measured J-editing results for dodecane and a fit therefor.

FIG. 21 shows the measured results of an experiment to generate a J-modulation curve of dodecane. The experimental parameters included $f_H$=1.535 MHz, $f_C$=386 kHz, $g_z$=11.5 G/cm, N=2, $N_E$=2500, $T_{E1}$=8.5 ms, $T_{E2}$=400 µs, $T_{90}$=16 is, $T_{acq}$=256 µs, and $N_{avg}$=32. The resulting curve is well-fit by a single cosine with J=122 Hz, in good agreement with the expected value of 125 Hz for C—H single bonds. These measurements show that single-bond heteronuclear J-coupling constants of natural abundance samples can be reliably measured in small and inhomogeneous static magnetic fields.

Figure 22:
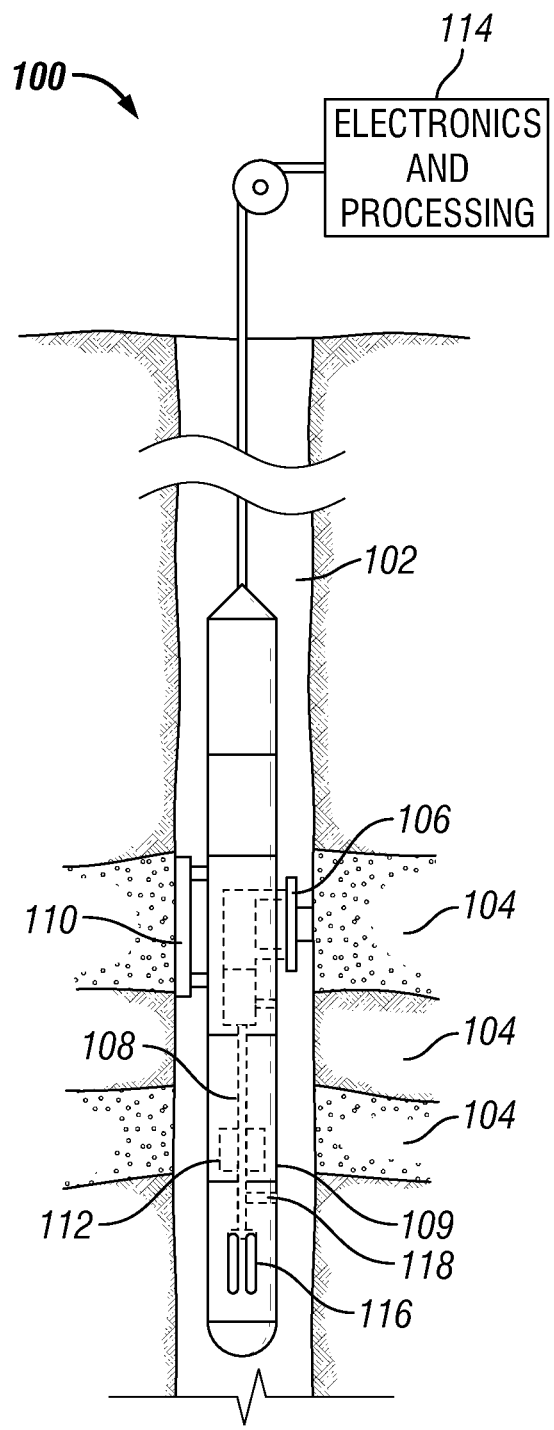
FIG. 22 is a schematic diagram of a wellbore tool for determining a composition of a formation fluid sample using J-editing techniques.

Turning to FIG. 22, a schematic diagram shows a wellbore tool 100 for determining composition of a formation fluid using J-editing techniques. In particular, the wellbore tool 100 determines mud contamination of a formation fluid using J-editing techniques.

In this example, the wellbore tool 100 is a wireline tool. The wireline tool 100 is disposed within a wellbore 102 that traverses a formation 104. The wireline tool includes 100 a formation fluid testing module, such as the Modular Formation Dynamics Tester™ (MDT) module of Schlumberger. The formation fluid testing module includes a selectively extendable fluid admitting assembly (e.g., probe) 106. This assembly 106 extends into contact with the formation 104 and withdraws formation fluid from the formation 104 (e.g., samples the formation). The fluid flows through the assembly 106 and into a flow line 108 within a housing 109 of the tool 100. A pump module (not shown) is used to withdraw the formation fluid from the formation 104 and pass the fluid through the flow line 108. An optical analyzer (not shown) can be used to conduct optical tests on the fluid within the flow line 108. The wireline tool 102 may also include a selectively extendable tool anchoring member 110 that is arranged to press the probe 106 assembly against the formation 104.

The wireline tool 100 also includes a NMR module 112 for analyzing at least a portion of the formation fluid in the flow line 108 (e.g., a hydrocarbon sample). The NMR module 112 includes an electro-magnetic device, such as a magnet or an array of magnets formed from a magnetic material. The electro-magnetic device is configured to induce a homogeneous static magnetic field in a portion of the fluid sample within the flow line 108. The NMR module 112 also includes a coil and NMR electronics that are configured (i) to apply an oscillating magnetic field to the fluid sample according to a J-editing pulse sequence and (ii) to make measurements by detecting a resulting signal. In one embodiment, the J-editing pulse sequence incorporates a chemically selective excitation pulse and the chemically selective excitation pulse is arranged to suppress signals other than signals at or about 150 Hz. In a further embodiment, the J-editing pulse sequence includes J-modulations scans with interleaved reference scans.

The wireline tool 100 may contain a processor or processors for processing measurements and generating one or more J-modulation curves from the detected signals and/or determining whether any J-encoding time signal at 150 Hz is detected, as described herein. Alternatively or in addition, a processor or processors 114 may be located uphole, and signals may be sent from the wireline tool 100 uphole for processing. The processor may be a programmed computer, a dedicated processor, a system of microprocessors or other circuitry capable of analyzing the NMR data obtained by NMR module 112 in order to generate one or more J-modulation curves and/or determine whether any J-encoding time signal at or about 150 Hz is detected.

After passing through the NMR module 112, the formation fluid (e.g., the hydrocarbon sample) may be pumped out of the flow line 108 and into the wellbore 102 through a port 118. Some of the formation fluid may also be passed to a fluid collection module 116 that includes chambers for collecting fluid samples and retaining samples of the formation fluid for subsequent transport and testing at the surface (e.g., at a testing facility or laboratory).

In illustrative embodiments, if a J-encoding time signal at 150 Hz is detected, the presence of a hydrocarbon having internal double bonds (e.g., olefin) is indicated. The presence of an olefin in the formation fluid taken from the formation 104 can be indicative of the presence of synthetic oil based mud (SBM) in the formation. The amplitude of the olefin signal can be used to determine the presence or concentration of contamination in the oil sample. The presence or concentration of contamination determined by the NMR module 112 and processor 114 may be reported to an operator or may be used to automatically control whether a fluid sample is kept for storage in the fluid collection module 116 or jettisoned into the wellbore 102 through the port 118. In this manner, samples obtained by the wireline tool 100 may be monitored for contamination and, when a sample containing an "acceptable" concentration of contamination is obtained, the sample may be stored in the fluid collection module 116 and brought uphole for further analysis. The acceptable concentration may be determined relative to a threshold value.

In further embodiments, the NMR module 112 of the wireline tool 100 may also be configured to conduct NMR spectroscopy experiments as disclosed in previously incorporated co-owned U.S. patent application Ser. No. 14/067,475 filed on Oct. 30, 2013. The NMR spectroscopy experiments may be used to confirm the findings of the J-editing analysis regarding the presence or lack thereof of olefins in a hydrocarbon sample. Also, the J-editing analysis may be used to confirm the finding of the NMR spectroscopy experiments regarding the presence or lack thereof of olefins in a hydrocarbon sample. Further details regarding downhole NMR systems that can perform NMR spectroscopy in a flow line can be found in U.S. Pat. No. 8,471,559, issued on Jun. 25, 2013, and U.S. Patent Application Publication No. 2012/0169334, published on Jul. 5, 2012. Each of these references is incorporated by reference herein in their entireties.

Figure 23:
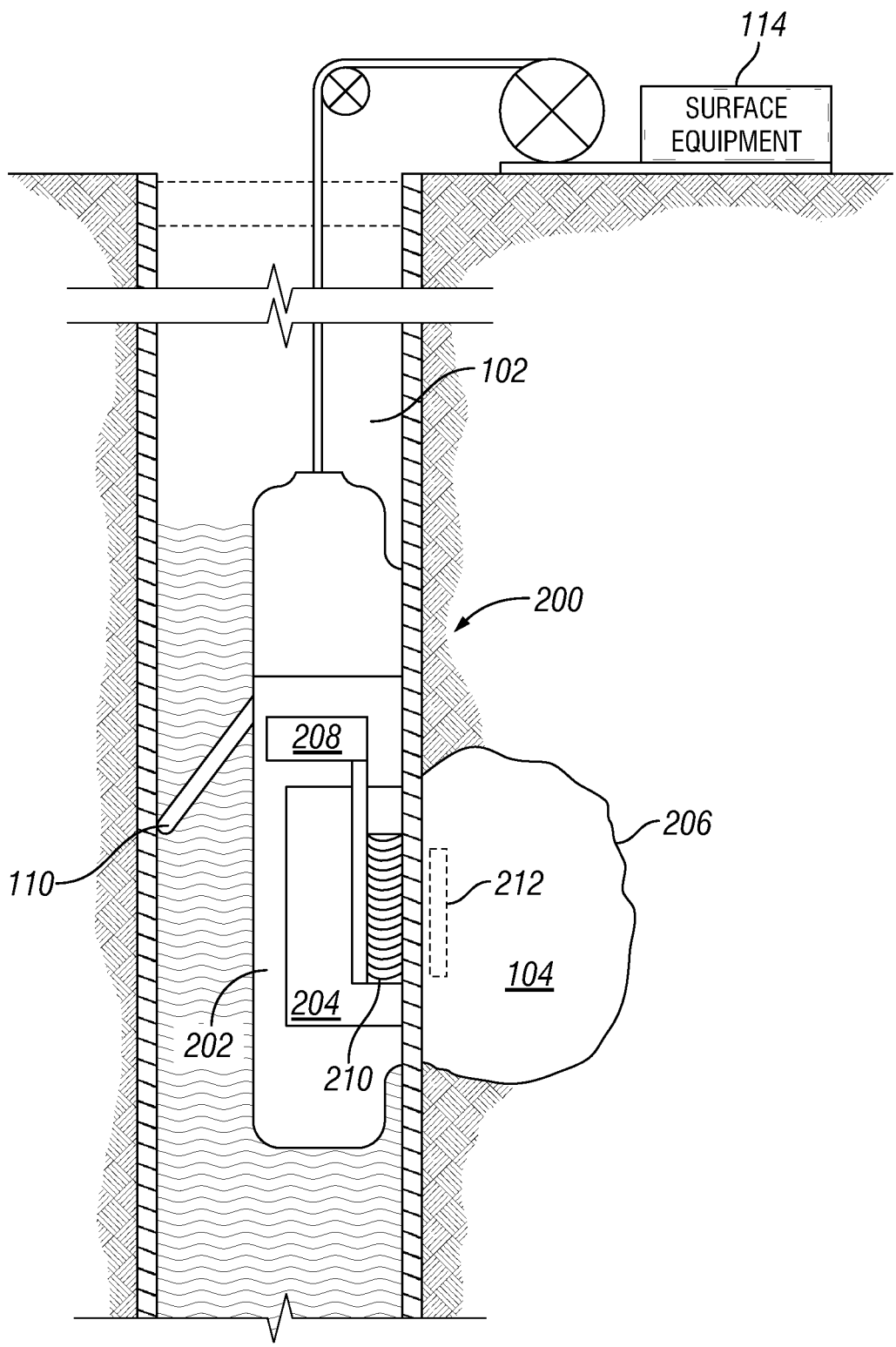
FIG. 23 is a schematic diagram of another wellbore tool for determining characteristics of a formation using J-editing techniques.

FIG. 23 shows another example of a wireline tool 200 for determining characteristics of a formation using J-editing techniques. The wireline tool 200 includes an NMR logging module 202 that is used to investigate, in situ, a formation 104 surrounding a wellbore 102 and to determine a characteristic of the formation (e.g., characteristics of solids and liquids within the formation). The NMR logging module 202 includes an electro-magnetic device 204 for applying an inhomogeneous static magnetic field to a sensitivity zone 206 within the formation 104. The NMR logging module 202 also includes at least one coil 208 and NMR electronics 210 electronically coupled to the coil. The coil 208 and NMR electronics 210 are configured (i) to apply an oscillating magnetic field to the formation according to a J-editing pulse sequence and (ii) to make measurements by detecting a resulting signal from an area of interest 212 within the formation. The methods and processes described above for inhomogeneous static magnetic fields ("fringe fields") can be used with such an implementation of the wireline tool 200.

The methods described herein can be implemented by various other wellbore tools and wellbore tool configurations. For example, the methods described herein can be implemented by a wellbore tool that is conveyed by other means, such coiled tubing. Furthermore, the methods described herein can also be applied in logging-while-drilling (LWD) operations, sampling-while-drilling operations, measuring-while-drilling operations, or any other operation where monitoring or logging of formation fluid is performed.

Furthermore, in some embodiments, the methods described herein are performed in a wellbore using a wellbore tool. In other embodiments, the methods described herein are performed at the surface using a laboratory NMR system on formation fluid that has been brought to the surface. Also, the methods described herein can be used to analyze a variety of different types of formation fluids. In particular, the methods can be used to analyze light oils, heavy oils, biodegraded oils, water washed oils, live oils, dead oils, gases, and water.

There have been described and illustrated herein several embodiments of methods of analyzing an oil sample by investigating J-couplings of an oil sample utilizing NMR J-editing techniques. While particular embodiments and aspects have been described, it is not intended that the disclosure be limited thereto, and it is intended that the claims be as broad in scope as the art will allow and that the specification be read likewise. Thus, while particular parameter values have been set forth for specific tests, it will be appreciated that other parameter values could be utilized. It will therefore be appreciated by those skilled in the art that yet other modifications could be made. Accordingly, all such modifications are intended to be included within the scope of this disclosure as defined in the following claims. In the claims, means-plus-function clauses, if any, are intended to cover the structures described herein as performing the recited function and not only structural equivalents, but also equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method of characterizing a hydrocarbon sample, comprising:
   subjecting the hydrocarbon sample to a pulse sequence that comprises a chemically selective nuclear magnetic resonance (NMR) pulse sequence portion and a detection pulse sequence portion with at least one π pulse; and
   analyzing NMR signals resulting from the subjecting to identify a J-coupling frequency present in at least one molecule of said hydrocarbon sample;
   wherein the chemically selective NMR pulse sequence portion comprises an initial pulse sequence of at least one introductory pulse followed by: (i) a spin pulse of (π) on an X channel at a time after the initial pulse sequence defined by a variable time delay J-encoding time (τ), and (ii) a spin pulse sequence of $(T_{E1}/2\text{-}(\pi)_x\text{-}T_{E1}/2)_N$-CPMG on an A channel, wherein N is an integer of at least 1 and the CPMG is a Carr-Purcell Meiboom Gill sequence with signal detection and having $N_E$ $(\pi)_x$ refocusing pulses and a period of $T_{E2}$, wherein $N_E$ is an integer equal to at least 1.

2. The method according to claim 1,
   wherein the subjecting comprises:
   inducing a magnetic field in the hydrocarbon sample; and
   applying an oscillating magnetic field to the hydrocarbon sample according to the chemically selective NMR pulse sequence portion, wherein the chemically selective NMR pulse sequence portion incorporates a chemically selective excitation pulse that preferentially selects spins satisfying particular conditions while suppressing other spins; and
   wherein the analyzing comprises:
   making measurements by detecting a resulting signal and processing the resulting signal.

3. The method according to claim 2, wherein the at least one molecule comprises a double bonded carbon atom.

4. The method according to claim 3, wherein the J-coupling frequency is approximately 150 Hz.

5. The method according to claim 1, wherein the initial pulse sequence comprises a π/4(x) pulse on the A channel, followed by a π(y) pulse on the A channel after time τ', followed by a 3π/4(−x) pulse on the A channel after additional time τ', and a π pulse on the X channel at the time of said π(y) pulse on the A channel.

6. The method according to claim 5, wherein the π pulse on the X channel at the time of the π(y) pulse on the A channel is a narrow-band pulse tuned to a desired frequency.

7. The method according to claim 5, wherein the initial pulse sequence comprises a π/2(y) pulse on the A channel.

8. The method according to claim 5, wherein the at least one molecule comprises an internal double bonded carbon atom, the J-coupling frequency is approximately 150 Hz, and τ' is chosen as n/2(150 Hz), wherein n is an odd integer equal to at least 1.

9. The method according to claim 5, wherein the at least one molecule comprises a double-bonded carbon atom, the J-coupling frequency is approximately 160 Hz, and τ' is chosen as n/2(160 Hz), wherein n is an odd integer equal to at least 1.

10. The method according to 5, wherein the at least one molecule contains a single-bonded carbon atom, the J-coupling frequency is approximately 125 Hz, and τ' is chosen as n/2(125 Hz), wherein n is an odd integer equal to at least 1.

11. The method according to claim 1, wherein the A channel is configured to cause $^1H$ spins and the X channel is configured to cause $^{13}C$ spins.

12. The method according to claim 1, wherein N=2, and $T_{E1} \approx 6\tau$.

13. The method according to claim 4, wherein
the hydrocarbon sample is taken from an earth formation by a wellbore tool,
the subjecting is done by the wellbore tool in a wellbore traversing the earth formation, and
the method further comprises determining a concentration of synthetic based mud (SBM) contamination in the hydrocarbon sample based on the analyzing.

14. The method according to claim 13, further comprising:
jettisoning the hydrocarbon sample downhole based on the concentration of the SBM contamination in the hydrocarbon sample.

15. The method according to claim 13, further comprising:
storing the hydrocarbon sample in the wellbore tool based on the concentration of the SBM contamination in the hydrocarbon sample.

16. The method according to claim 2, wherein the at least one molecule comprises a triple bonded carbon atom.

17. The method according to claim 16, further comprising measuring an amount of triple bonded carbon to determine an amount of molecules with triple bonds in the hydrocarbon sample.

18. The method according to claim 1, wherein the J-coupling frequency is approximately 250 Hz.

19. A method of characterizing a hydrocarbon sample, comprising:
subjecting the hydrocarbon sample to a pulse sequence that comprises a chemically selective nuclear magnetic resonance (NMR) pulse sequence portion and a detection pulse sequence portion with at least one $\pi$ pulse; and
analyzing NMR signals resulting from the subjecting to identify a J-coupling frequency present in at least one molecule of said hydrocarbon sample;
wherein the chemically selective nuclear magnetic resonance (NMR) pulse sequence includes J-modulation scans interleaved with reference scans, wherein each J-modulation scan includes an initial pulse sequence of at least one introductory pulse followed by: (i) a spin pulse of ($\pi$) on an X channel at a time after said initial pulse sequence defined by a variable time delay J-encoding time ($\tau$), and (ii) a spin pulse sequence of $(T_{E1}/2\text{-}(\pi)_x\text{-}T_{E1}/2)_N$-CPMG on an A channel, wherein N is an integer of at least 1 and CPMG is a Carr-Purcell Meiboom Gill sequence with signal detection and having $N_E$ $(\pi)_x$ refocusing pulses and a period of $T_{E2}$, wherein $N_E$ is an integer equal to at least 1, and each reference scan includes in initial pulse sequence of at least one introductory pulse followed by a spin pulse sequence of $(T_{E1}/2\text{-}(\pi)_x\text{-}T_{E1}/2)_N$-CPMG on the A channel and no spin pulses on the X channel.

20. An apparatus for characterizing a hydrocarbon sample, the apparatus comprising:
a nuclear magnetic resonance (NMR) module for subjecting the hydrocarbon sample to a pulse sequence that contains a chemically selective nuclear magnetic resonance pulse sequence portion and a detection pulse sequence portion with at least one $\pi$ pulse, and for making measurements by detecting resulting NMR signals; and
a processor coupled to the NMR modules and configured to use the measurements and identify therefrom a J-coupling frequency present in at least one molecule of said hydrocarbon sample;
wherein the chemically selective NMR pulse sequence portion comprises an initial pulse sequence of at least one introductory pulse followed by: (i) a spin pulse of ($\pi$) on an X channel at a time after the initial pulse sequence defined by a variable time delay J-encoding time ($\tau$), and (ii) a spin pulse sequence of $(T_{E1}/2\text{-}(\pi)_x\text{-}T_{E1}/2)_N$-CPMG on an A channel, wherein N is an integer of at least 1 and the CPMG is a Carr-Purcell Meiboom Gill sequence with signal detection and having $N_E$ $(\pi)_x$ refocusing pulses and a period of $T_{E2}$, wherein $N_E$ is an integer equal to at least 1.

21. The apparatus according to claim 20, wherein the NMR module comprises:
an electro-magnetic device for inducing a static magnetic field in the hydrocarbon sample, and
a coil for applying an oscillating magnetic field to the hydrocarbon sample according to the chemically selective NMR pulse sequence portion.

22. The apparatus according to claim 20, wherein the chemically selective NMR pulse sequence portion incorporates a chemically selective excitation pulse that preferentially selects spins satisfying particular conditions while suppressing other spins.

* * * * *